United States Patent
Swift et al.

(10) Patent No.: US 10,166,358 B2
(45) Date of Patent: Jan. 1, 2019

(54) MASK ASSEMBLY SUPPORTING ARRANGEMENTS

(71) Applicant: ResMed Limited, Bella Vista, New South Wales (AU)

(72) Inventors: Lance Ian Swift, Sydney (AU); Craig David Edwards, Sydney (AU)

(73) Assignee: ResMed Limited, Bella Vista (AU)

(*) Notice: Subject to any disclaimer, the term of this patent is extended or adjusted under 35 U.S.C. 154(b) by 468 days.

(21) Appl. No.: 14/941,953

(22) Filed: Nov. 16, 2015

(65) Prior Publication Data

US 2016/0106945 A1   Apr. 21, 2016

Related U.S. Application Data

(63) Continuation of application No. 13/484,419, filed on May 31, 2012, now Pat. No. 9,211,388.

(60) Provisional application No. 61/527,837, filed on Aug. 26, 2011, provisional application No. 61/457,769, filed on May 31, 2011.

(51) Int. Cl.
  *A61M 16/06* (2006.01)
  *A61M 16/00* (2006.01)

(52) U.S. Cl.
  CPC .... *A61M 16/0683* (2013.01); *A61M 16/0057* (2013.01); *A61M 16/06* (2013.01); *A61M 16/0622* (2014.02); *A61M 16/0666* (2013.01); *A61M 2209/088* (2013.01); *A61M 2210/0618* (2013.01); *A61M 2210/0662* (2013.01)

(58) Field of Classification Search
  CPC .. A61M 16/00; A61M 16/0488; A61M 16/06; A61M 16/0683; A61M 2209/088; A61M 2210/0662; B63C 11/12
  USPC ........... 128/203.29, 204.18, 205.25, 206.12, 128/206.13, 206.21, 206.27, 206.28, 128/207.11, 207.13, 207.14, 207.17
  See application file for complete search history.

(56) References Cited

U.S. PATENT DOCUMENTS

| 1,216,881 A | 2/1917 | Tabler |
| 3,457,564 A | 7/1969 | Holloway |

(Continued)

FOREIGN PATENT DOCUMENTS

| CH | 700500 B1 * | 9/2010 | ........ A61M 16/0683 |
| EP | 2022528 | 2/2009 | |

(Continued)

OTHER PUBLICATIONS

Extended European Search Report for corresponding EP Application No. 12170279, dated Aug. 31, 2012, 8 pages.

(Continued)

*Primary Examiner* — (Jackie) Tan-Uyen T Ho
*Assistant Examiner* — Joseph D Boecker
(74) *Attorney, Agent, or Firm* — Nixon & Vanderhye P.C.

(57) ABSTRACT

A mask assembly includes nasal interface, e.g., in the form of a pair of nozzles, at least one joining portion provided to each side of the nasal interface, and a headgear coupled or otherwise provided to or extending from the joining portion, that is looped around the patient's ears. The joining portion is small and compact and may be readily affixed to an existing nasal arrangement, i.e., retrofitted. The joining portion and the headgear can be formed in separate components, or they can be formed as an integral or one-piece arrangement.

14 Claims, 30 Drawing Sheets

(56) References Cited

U.S. PATENT DOCUMENTS

| | | | |
|---|---|---|---|
| 5,724,965 A * | 3/1998 | Handke | A61M 16/06 128/205.25 |
| 7,861,715 B2 | 1/2011 | Jones | |
| 8,025,057 B2 | 9/2011 | Ging et al. | |
| 8,479,736 B2 | 7/2013 | Ging et al. | |
| 8,636,007 B2 | 1/2014 | Rummery et al. | |
| 8,985,117 B2 | 3/2015 | Gunaratnam | |
| 9,211,388 B2 * | 12/2015 | Swift | A61M 16/06 |
| 2002/0117177 A1 * | 8/2002 | Kwok | A61M 16/06 128/207.11 |
| 2003/0150460 A1 | 8/2003 | Campbell et al. | |
| 2003/0183227 A1 * | 10/2003 | Klemperer | A61M 16/06 128/201.26 |
| 2003/0186024 A1 | 10/2003 | Walsh | |
| 2005/0109342 A1 * | 5/2005 | Easom | A61M 16/0683 128/206.12 |
| 2008/0190432 A1 * | 8/2008 | Blochlinger | A61M 16/06 128/205.25 |
| 2009/0032026 A1 | 2/2009 | Price et al. | |
| 2009/0044809 A1 | 2/2009 | Welchel et al. | |
| 2010/0000534 A1 | 1/2010 | Kooij et al. | |
| 2010/0037897 A1 | 2/2010 | Wood | |
| 2010/0206312 A1 * | 8/2010 | O'Leary | A61M 16/0666 128/207.18 |
| 2010/0229868 A1 | 9/2010 | Rummery et al. | |
| 2010/0258132 A1 | 10/2010 | Moore | |
| 2011/0067704 A1 | 3/2011 | Kooij et al. | |
| 2011/0247627 A1 | 10/2011 | Omura et al. | |
| 2012/0304999 A1 | 12/2012 | Swift et al. | |
| 2013/0152938 A1 | 6/2013 | Jablonski | |
| 2014/0013552 A1 | 1/2014 | Liang et al. | |

FOREIGN PATENT DOCUMENTS

| | | |
|---|---|---|
| WO | WO 2008/019294 | 2/2008 |
| WO | WO 2008/106716 | 9/2008 |
| WO | WO 2009/052560 | 4/2009 |
| WO | WO 2009/109005 | 9/2009 |

OTHER PUBLICATIONS

European Patent Office Communication for corresponding EP 12 170 279.9, dated Nov. 6, 2013, 5 pages.

* cited by examiner

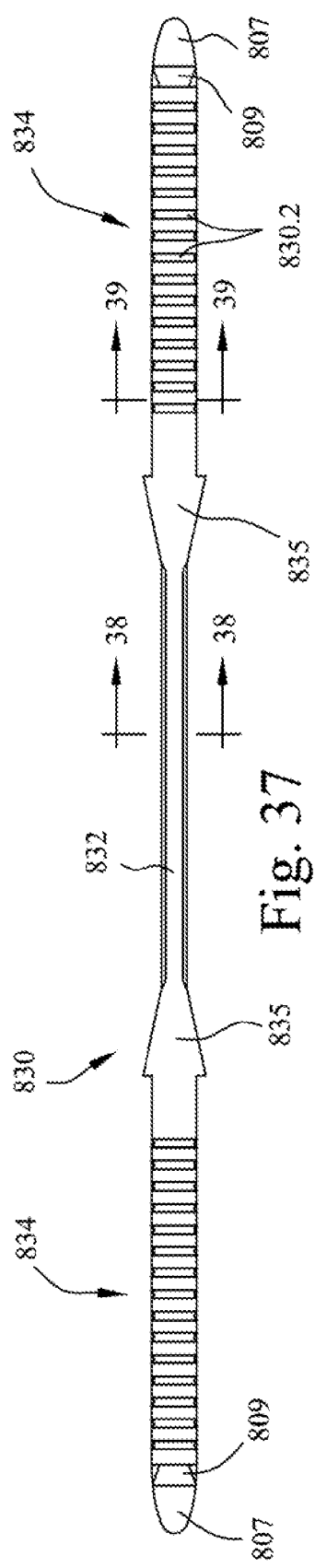
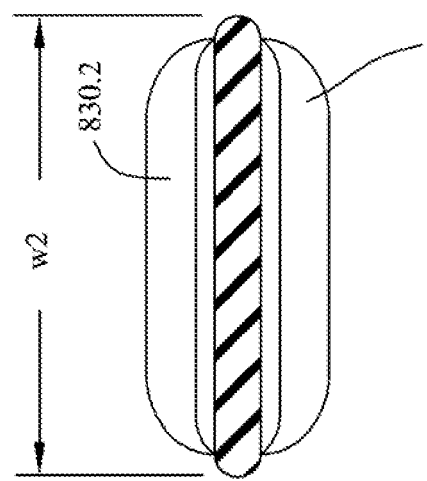
Fig. 39
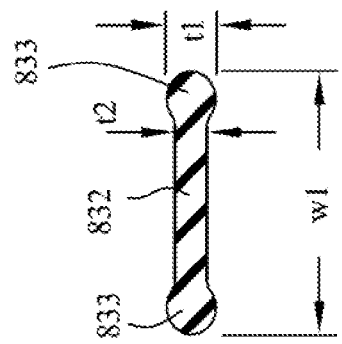
Fig. 38
Fig. 37

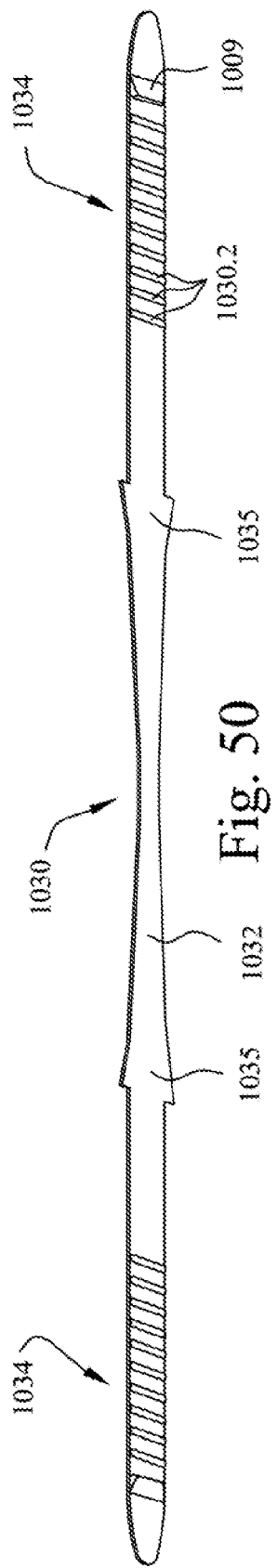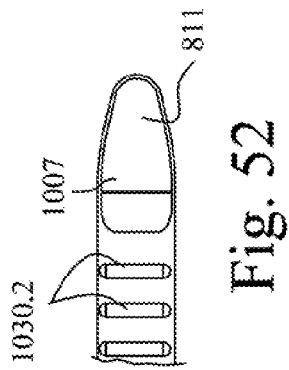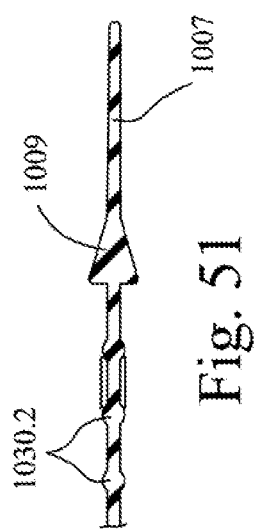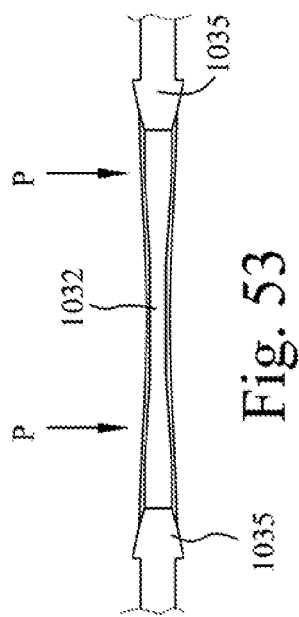

USE MASK ASSEMBLY SUPPORTING ARRANGEMENTS

CROSS-REFERENCE TO RELATED APPLICATIONS

This application is a continuation of U.S. application Ser. No. 13/484,419, filed May 31, 2012, which claims the benefit of U.S. Provisional Application No. 61/457,769, filed May 31, 2011, and U.S. Provisional Application No. 61/527,837, filed Aug. 26, 2011 each incorporated herein by reference in its entirety.

FIELD OF TECHNOLOGY

The present technology relates to a mask assembly, and a headgear assembly for supporting a mask.

BACKGROUND OF TECHNOLOGY

Treatment of obstructive sleep apnea (OSA) by the application of positive airway pressure (PAP) involves the application of a flow of pressurized breathable gas (typically room air) to either the nose or the nose and mouth of a patient while he sleeps. The technique is said to "splint" open the airways. Typical treatment pressures are in the range of about 4 to about 20 cm $H_2O$ (with typical treatment pressures of about 4-14 or 8-12 cm $H_2O$, or about 10 cm $H_2O$), with flows of approximately 200 liters per minute. The flow of pressurized air is produced by a blower and delivered to the patient via a patient interface. The blower and patient interface are typically joined by a conduit. Patient interface arrangements include a nasal mask, nose and mouth mask, nasal prongs and nasal pillows or nozzles and combinations thereof. In all forms of patient interface used with PAP for treating sleep disordered breathing or snoring, there is usually a need to counter balance the force of pressurized air and to correctly position the interface. Typically this is done with a headgear arrangement.

SUMMARY OF TECHNOLOGY

One aspect of the present technology is directed toward providing a mask assembly and a headgear arrangement for supporting a mask for the use of treatment of sleep disordered breathing which improves patient comfort, is long lasting, has a low visual impact, does not obstruct the patient's field of view and/or fits a wide range of head shapes and sizes.

Another aspect of the present technology relates to a headgear that loops around the patient's ears and/or is readily removably attachable with a nasal interface.

Another aspect of the present technology is directed to a nasal interface, e.g., cannula, nozzles, pillows or puffs, prongs, nasal-only cushion, nasal-oro cushion, or combinations thereof, at least one joining portion, or a joining portion for each side of the nasal interface, that is repeatedly attachable to and detachable from the nasal interface; and a strap portion coupled or otherwise provided or extending from the joining portion, e.g., that is looped around the patient's ears. Each strap portion may be associated with a sleeve for added comfort to the patient. Each strap portion may include a stop to maintain the sleeve in place, e.g., to prevent excessive sliding towards the patient's ears.

Another aspect of the present technology is directed to a mask system for treating a wearer having a breathing disorder with gas pressurized above atmospheric pressure, the mask system comprising: a nasal interface having a seal portion to seal with at least one airway of the wearer, and at least a first lug formed in one piece of common material with the seal portion; at least a first joining portion having a receiving portion to detachably receive the first lug, and at least a first upper slot and a first lower slot; and headgear having at least a first strap with a first end that is threaded through the first upper slot and a second end that is threaded through the first lower slot, the headgear having a rear portion that is structured and dimensioned to be secured to the wearer's ear in use.

Another aspect of the present technology is directed to a headgear assembly for supporting a patient interface for treating a wearer having a breathing disorder with gas pressurized above atmospheric pressure, the headgear assembly comprising: at least a first joining portion having a receiving portion to detachably receive a first lug of a patient interface, and at least a first upper slot and a first lower slot; and headgear having at least a first strap with a first end that is threaded through the first upper slot and a second end that is threaded through the first lower slot, the headgear having a rear portion that is structured and dimensioned to be secured to the wearer's ear in use.

Another aspect of the present technology is directed to a headgear assembly for supporting a patient interface for treating a wearer having a breathing disorder with gas pressurized above atmospheric pressure, the headgear assembly comprising: at least a first joining portion having an attaching portion to detachably attach to a nasal interface, and at least a slot; and headgear having at least a first strap with a first end that is threaded through the slot and a second end that is attached to the first joining portion, the headgear having a rear portion that is structured and dimensioned to be secured to the wearer's ear in use.

Another aspect of the present technology is directed to a headgear assembly for supporting a patient interface for treating a wearer having a breathing disorder with gas pressurized above atmospheric pressure, the headgear assembly comprising: first and second joining portions each having an attaching portion to attach to a patient interface, each of the first and second joining portions having at least a first upper slot and a first lower slot; and headgear having a first strap and a second strap, independent from the first strap, each of the first and second straps having a first end that is threaded through the first upper slot and a second end that is threaded through the first lower slot of the respective first and second joining portions, each of the first and second straps having a rear portion structured and dimensioned to be secured to the wearer's ear in use.

Another aspect of the present technology is directed to a headgear assembly for supporting a patient interface for treating a wearer having a breathing disorder with gas pressurized above atmospheric pressure, the headgear assembly comprising: at least a first joining portion having an engagement portion attachable to and detachable from a patient interface, and at least a first common slot; and headgear having at least a first strap with a first end that is threaded through the common slot and a second end that is threaded through the common slot, the headgear having a rear portion that is structured and dimensioned to be secured to the wearer's ear in use.

Another aspect of the present technology is directed to a headgear assembly for supporting a patient interface for treating a wearer having a breathing disorder with gas pressurized above atmospheric pressure, the headgear assembly comprising: at least a first joining portion having an attaching portion to detachably attach to a patient interface; and headgear having first and second strap portions each having a respective first end extending from the first joining portion, one of the first or second strap portions having a second end with a slotted connector, and another of the first and second strap portions having a second end that is threaded through the slotted connector in a length adjustable manner, wherein a portion of the first and/or second strap portions has a first rear portion that is structured and dimensioned to be secured to the wearer's ear in use.

Another aspect of the present technology is directed to a mask system for treating a wearer having a breathing disorder with gas pressurized above atmospheric pressure, the mask system comprising: a nasal interface having a seal portion to seal with at least one airway of the wearer, and at least a first attachment portion formed in one piece of common material with the seal portion; at least a first joining portion having an attaching portion to detachably attach to the first attachment portion, and at least a first slot portion; and headgear having at least a first strap with a first end that is threaded through the first slot, the headgear having a rear portion that is structured and dimensioned to be secured to the wearer's ear in use.

Another aspect of the present technology is directed to a method for changing headgear on a mask assembly that includes a first headgear arrangement for supporting a mask, the method comprising: replacing the first headgear arrangement with a second headgear arrangement to support the mask in a fundamentally different way than the first headgear arrangement. In this manner, the existing first headgear arrangement, e.g. one that requires wrapping around the head, can be retroactively replaced with the second headgear arrangement, e.g., one that wraps around the ears, which may provide a viable alternative to the wearer (for temporary relief of discomfort resulting from repetitive application of forces/pressure to the same regions of the face/head) and may improve compliance as the alternative headgear may be associated with different points of application and therefore at least temporarily more comfortable. In a variant, a mask kit may be sold that includes both types of headgear arrangement so the wearer can alternate between the two or simply choose the one that best suits the wearer's needs. Such a kit may include a plurality of different nasal interfaces that will further multiply the wearer's ability to choose different combinations of components and keep discomfort to a minimum.

Another aspect of the present technology relates to a mask system for treating a wearer having a breathing disorder with gas pressurized above atmospheric pressure, the mask system comprising a nasal interface having a seal portion to seal with at least one airway of the wearer; and headgear having at least a first strap structured and dimensioned to be secured to the wearer's ear in use, the first strap having cheek portion adapted to contact the patient's cheek and an ear portion adapted to engage a rear portion the patient's ear, the cheek and ear portions having different profiles, dimensions, shapes and/or characteristics.

Yet another aspect of the present technology relates to a mask system for treating a wearer having a breathing disorder with gas pressurized above atmospheric pressure, the mask system comprising a nasal interface having a seal portion to seal with at least one airway of the wearer, and at least a first attachment portion; at least a first joining portion; and headgear having at least a first strap with a first end that is attached to the first joining portion, the headgear having a rear portion that is structured and dimensioned to be secured to the wearer's ear.

Other aspects, features, and advantages of this technology will become apparent from the following detailed description when taken in conjunction with the accompanying drawings, which are a part of this disclosure and which illustrate, by way of example, principles of this technology.

BRIEF DESCRIPTION OF THE DRAWINGS

The accompanying drawings facilitate an understanding of the various examples of this technology. In such drawings:

FIGS. 35-40 illustrate a mask assembly according to yet another variant of the present technology;

FIGS. 50-53 illustrate an ear-gear strap according to a variant of the present technology, where FIG. 51 is a cross-section towards the end portions of the strap of FIG. 50;

DETAILED DESCRIPTION

The following description is provided in relation to several examples which may share one or more common characteristics and features. It is to be understood that one or more features of any one example may be combinable with one or more features of one or more of the other examples. In addition, any single feature or combination of features in any of the examples may constitute additional subject matter that may be independently protected.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen. It is also acknowledged that the blowers described herein may be designed to pump fluids other than air.

Figure 22:
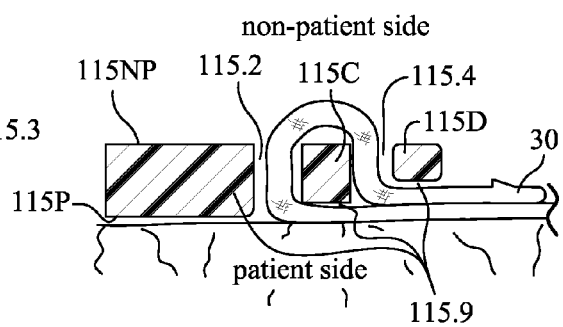
FIG. 22 is a schematic cross-section taken along line 22-22 of FIG. 21.
Figure 23:
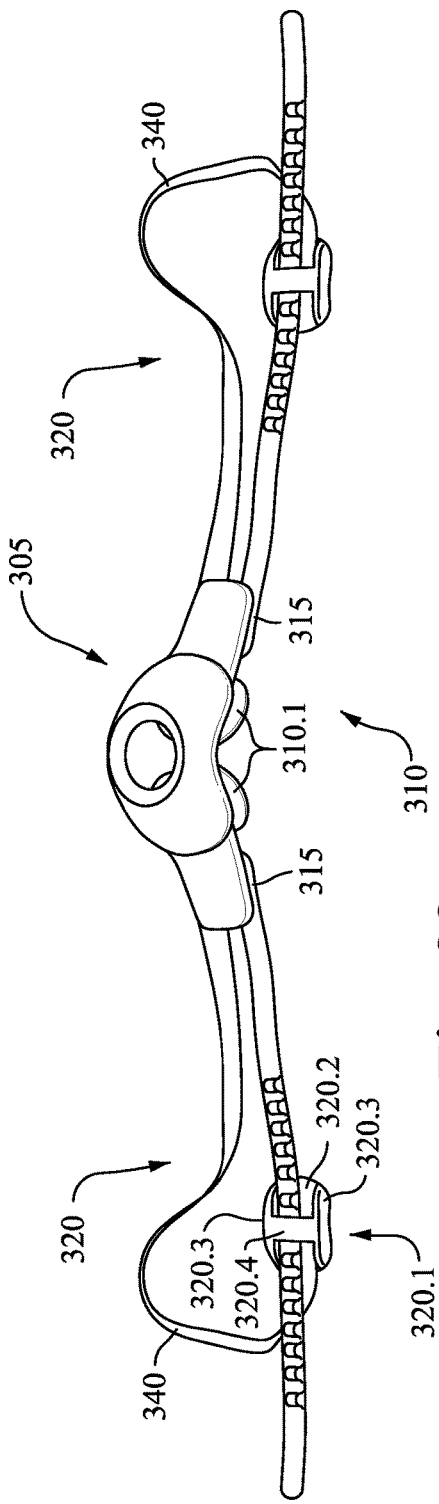
FIG. 23 is a perspective view of a mask assembly according to an example of the present technology.
Figure 24:
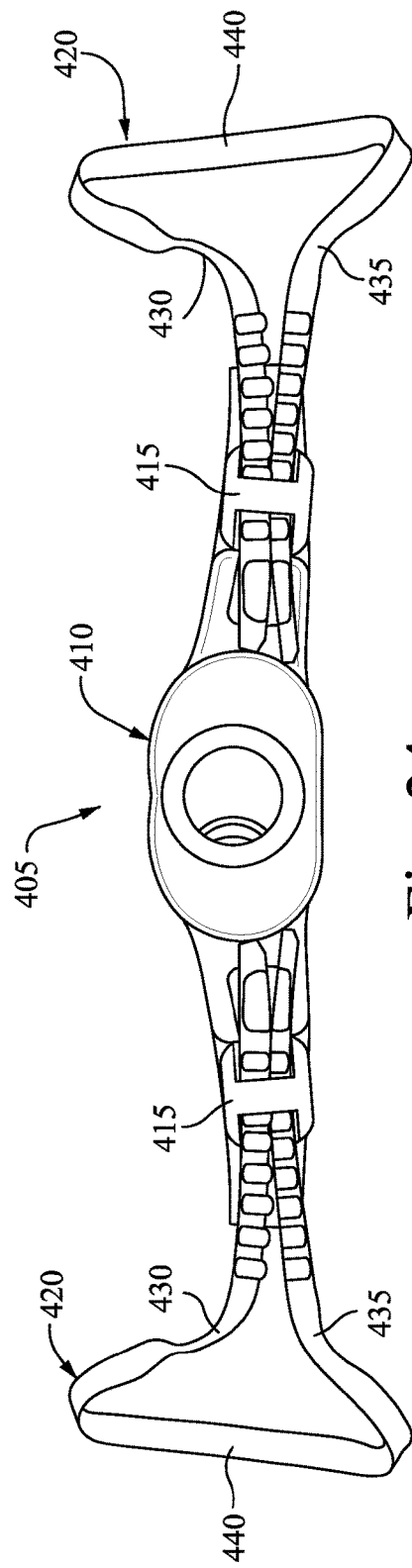
FIG. 24 is a rear view of a mask assembly according to an example of the present technology.
Figure 25:
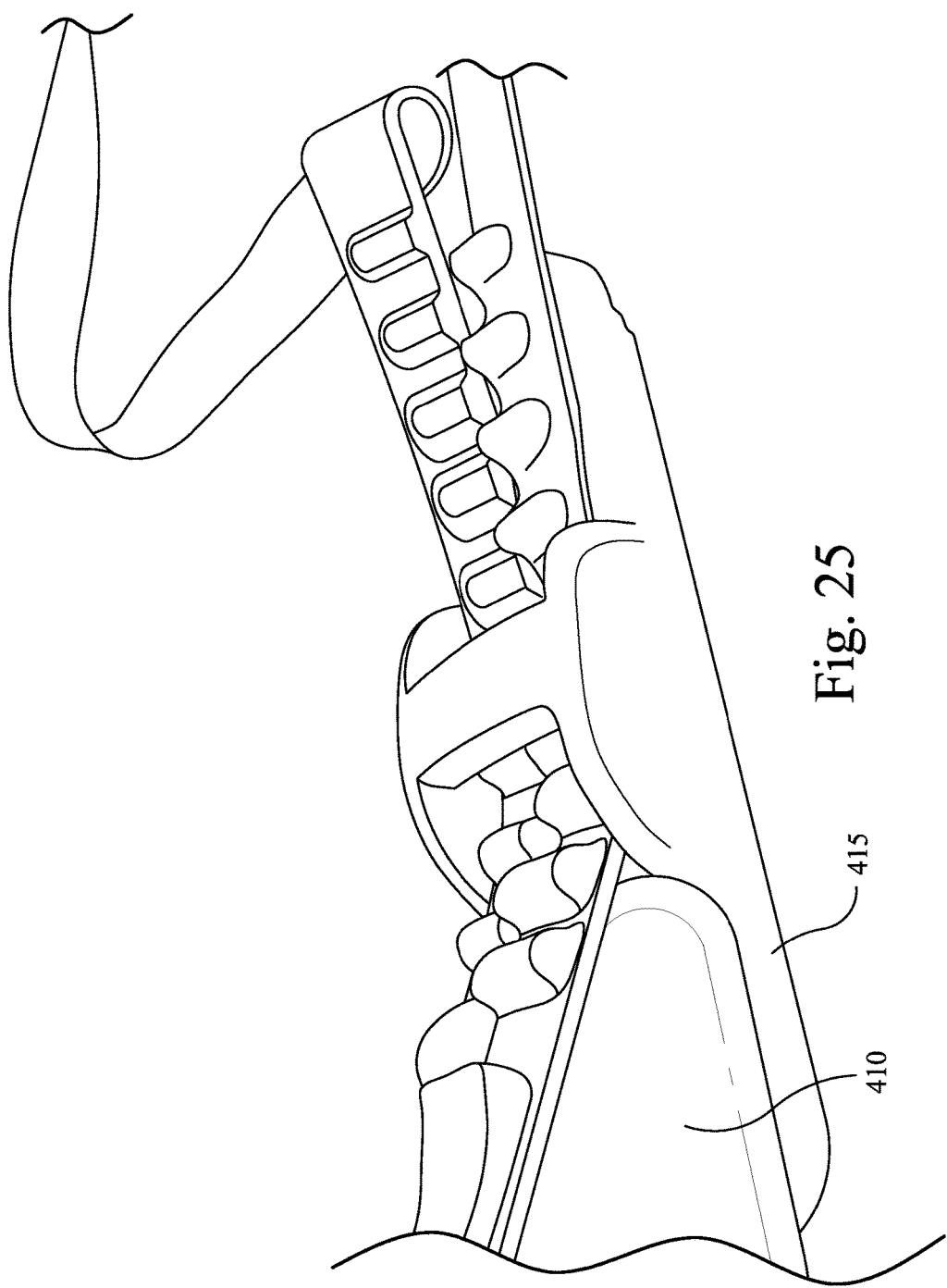
FIG. 25 is a partial perspective view of a portion of the mask assembly shown in FIG. 24.
Figure 26:
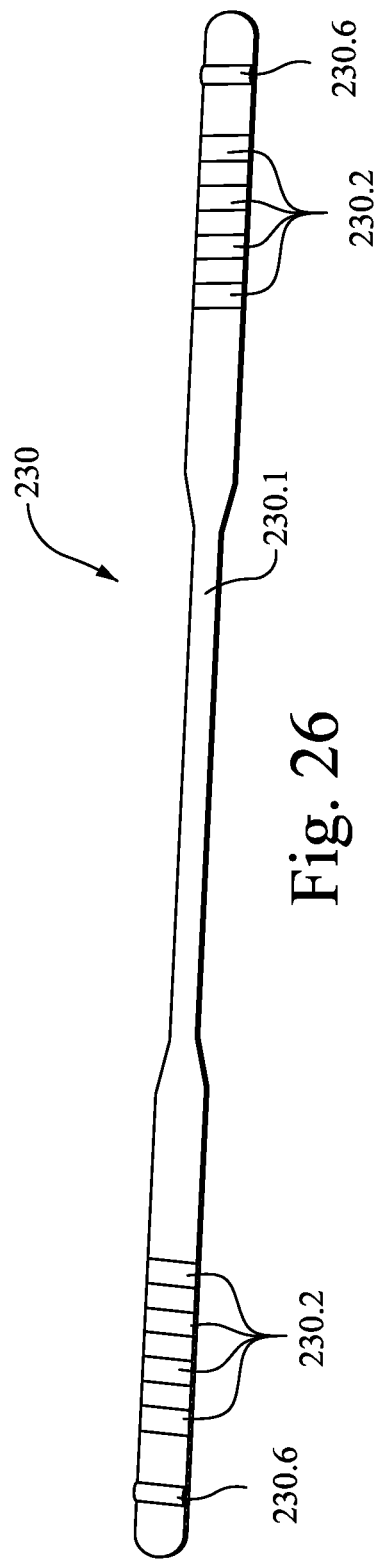
FIG. 26 illustrates a strap that may be used in the arrangement shown in FIGS. 24 and 25.

In the following description, a first main example is described in relation to FIGS. 1-12, FIGS. 13-22 illustrate a second main example, FIGS. 23-25 illustrate variants, FIG. 26 illustrates a strap that may be used in the variant of FIGS. 24 and 25 and possibly others, and FIGS. 27 and 28 describe yet another variant of the mask assembly. FIGS. 29-58 illustrate further variants and examples of the present technology.

Each main example and variant mask assembly includes a nasal interface, a joining portion and a headgear portion. In the examples provided, the nasal interface is in the form of ResMed's Swift FX™ nasal interface, which is generally described in relation to PCT International Application No. PCT/AU2008/001557, incorporated herein by reference in its entirety. The nasal interface in ResMed's Swift FX™ includes a pair of nozzles, pillows or nasal puffs, although the nasal interface could also be in the form of nasal prongs, a nasal-only cushion, a nasal-oro cushion, or combinations thereof. Such a mask is suitable for use with positive airway pressure for treatment of snoring, sleep apnea, or other sleeping disorders, and can be treated with a pressurized gas which is pressurized in the range of about 4-20 cm $H_2O$, with about 8-10 cm $H_2O$ being a typical pressure treatment range.

In the main example shown in FIGS. 1-12, mask assembly 5 includes a nasal interface 10, at least one and preferably multiple, e.g., a pair of joining portions 15, and a headgear 20 provided to each joining portion. In the example shown, the headgear associated with the left and right joining portions are independent from one another, although the headgear could be connected to one another along the back of the patient's head.

The headgear 20 is in the form of "ear-gear" to support the nasal interface on the patient's head. The "ear-gear" can be particularly useful in supporting cannula, prong, nozzle or puff-type nasal interfaces or full face masks. Moreover, such "ear-gear" is of less weight and/or helps the patient with hair management issues and to minimize contact with the top/rear portions of the patient's head, which may help avoid any perception that the headgear is causing hair loss (due to contact with the hair). Such "ear-gear" may also help to avoid discomfort caused by headgear that fits over and/or behind the patient's head, e.g., due to medical conditions and/or head shape, etc. Generally, the "ear-gear" strap may include a strap portion having different profiles, dimensions, shapes and/or characteristics to best suit that part of the patient's head the various portions are intended to contact. Moreover, such "ear-gear" may simply provide a viable alternative to normal headgear, e.g., allow alternation between headgear and "ear-gear", such as seasonal swaps, e.g., full headgear in Winter, ear-gear in Summer.

Figure 3:
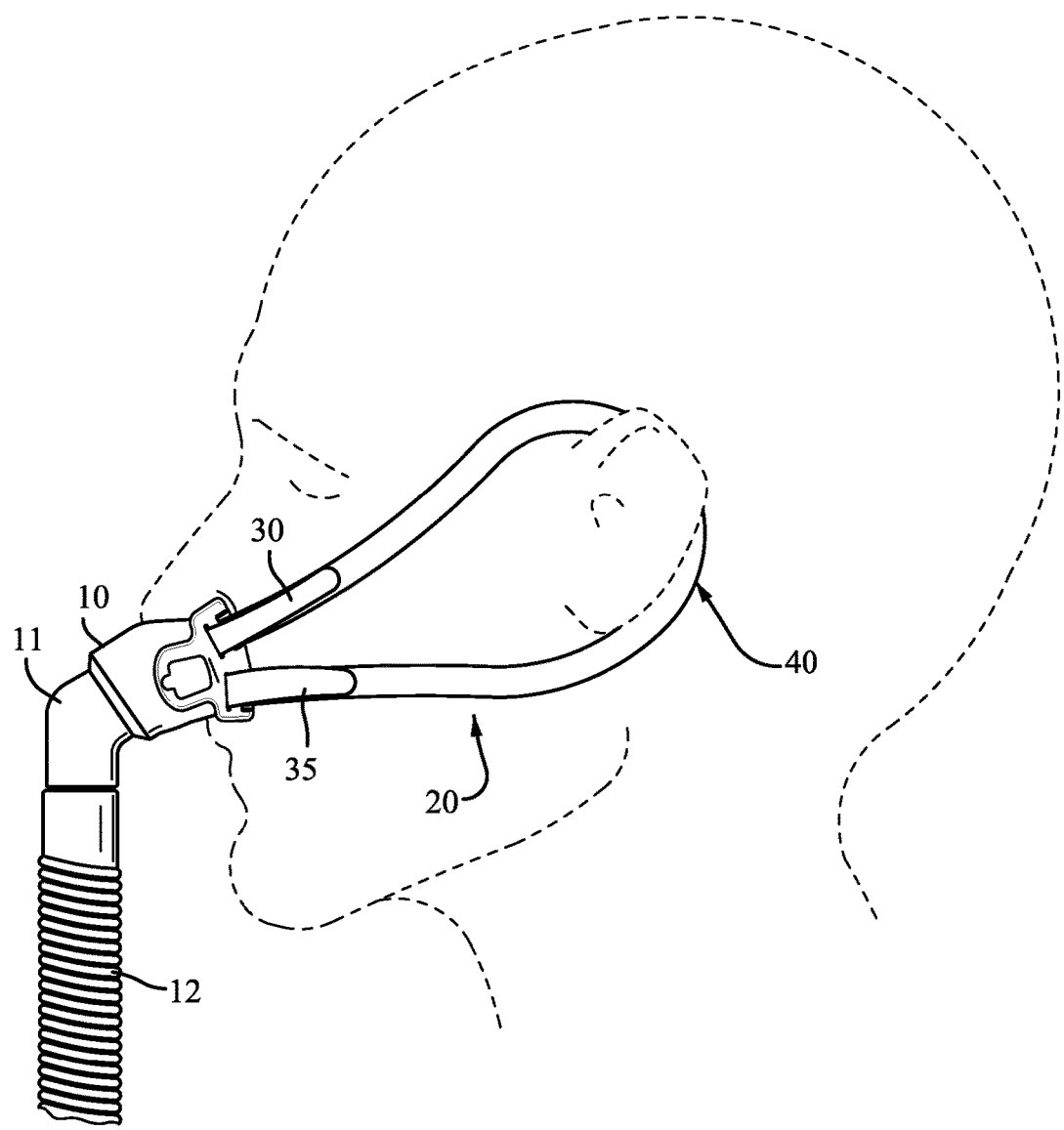
FIG. 3 is a side view of the mask assembly of FIG. 1 shown in position on a model patient's head.

Each headgear includes a first end 30 and a second end 35 which is intended to interface with a respective joining portion of the mask assembly. As shown in FIG. 3, each headgear includes a rear or ear portion 40 which is intended to loop around the ear of the patient. The headgear may include one or more, e.g., two, strap or strap portions, with a cheek portion to contact or otherwise overlie the patient's cheek. However, other headgear arrangements, such as those that may wrap around the back of the patient's head, are also possible. Further, as shown in FIG. 3, the mask assembly may include an elbow 11 as well as a "short" tube 12, which is intended to be coupled with a relatively larger air delivery tube which in turn is coupled to the flow generator.

Figure 4:
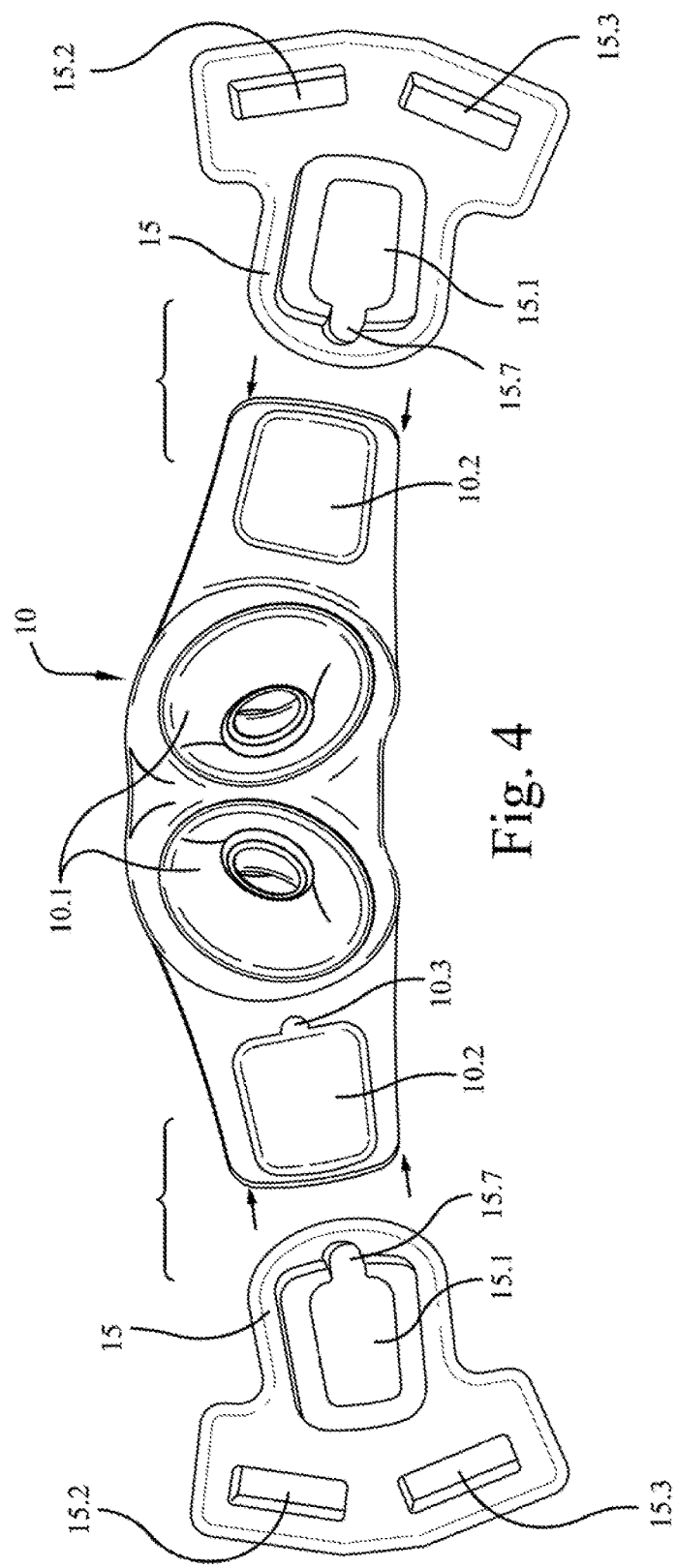
FIG. 4 is an exploded view of a subassembly of the nasal interface and joining portions according to an example of the present technology.
Figure 8:
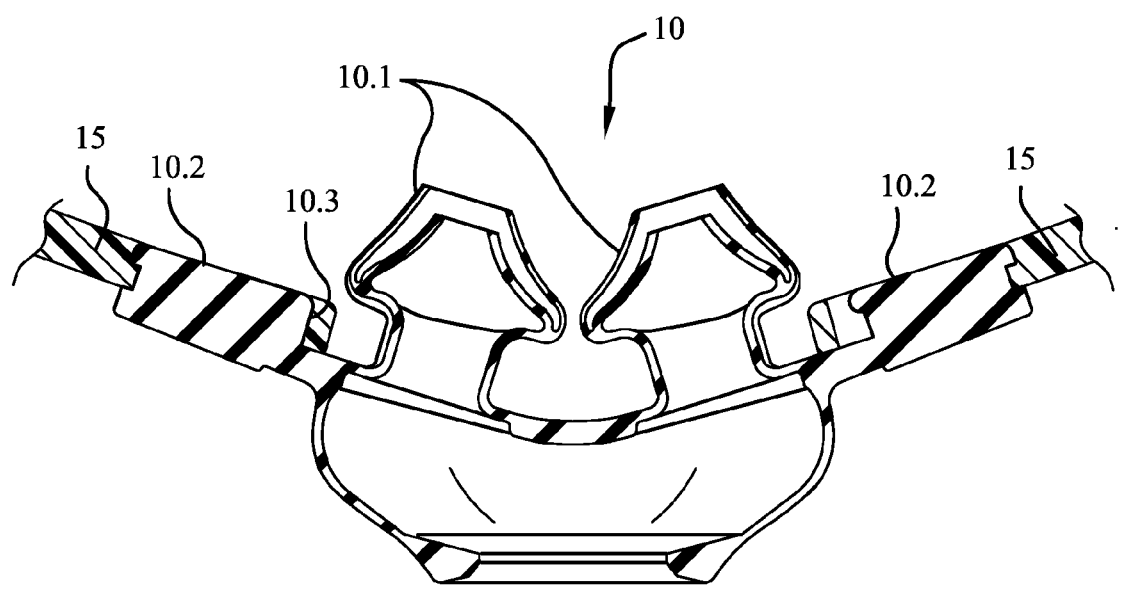
FIG. 8 is a cross-sectional view showing the subcombination of the nasal interface and joining portions shown in FIG. 4.
Figure 9:
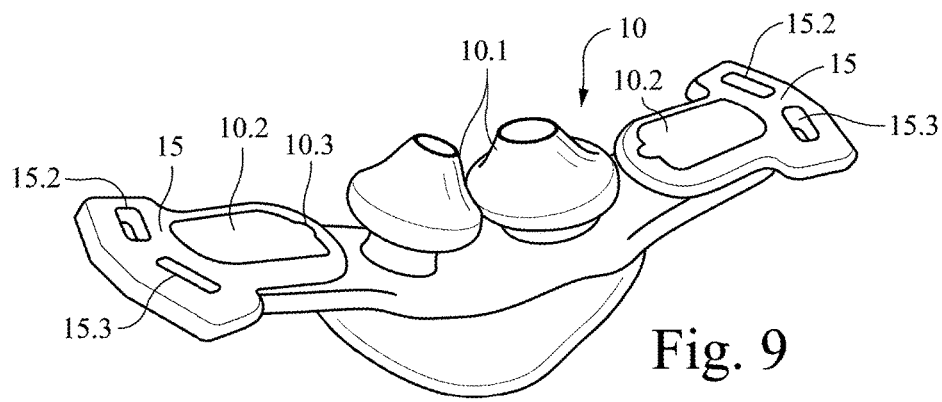
FIG. 9 is a perspective view of the subassembly of the nasal interface and joining portions.
Figure 10:
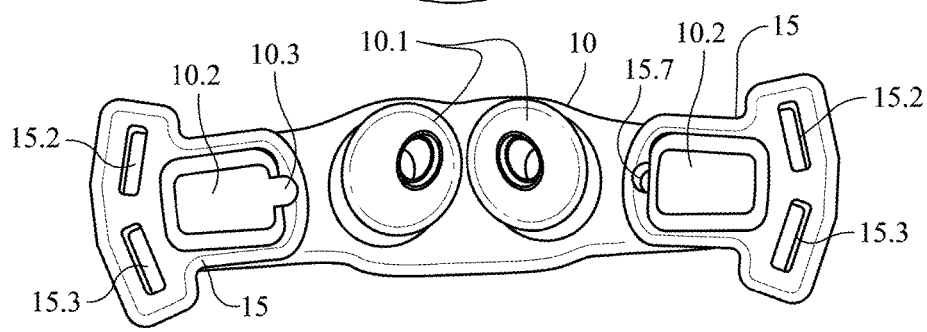
FIG. 10 is a front view of the subcombination of the nasal interface and the joining portions.
Figure 11:
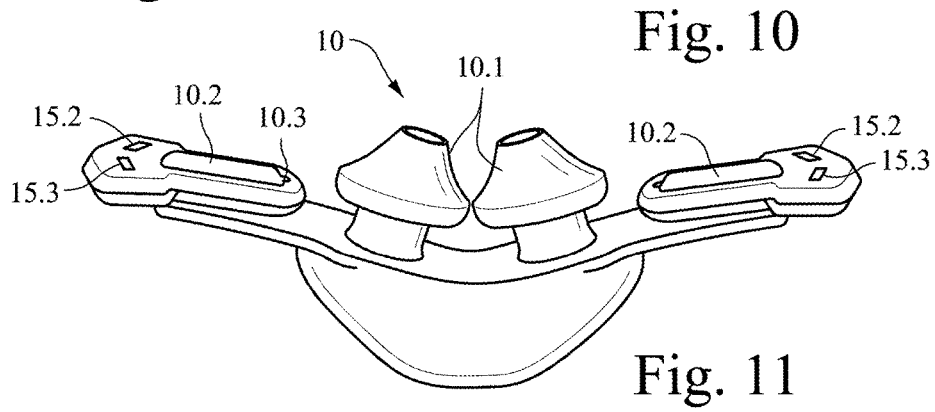
FIG. 11 is a bottom view of the subcombination of the nasal interface and joining portions.
Figure 12:
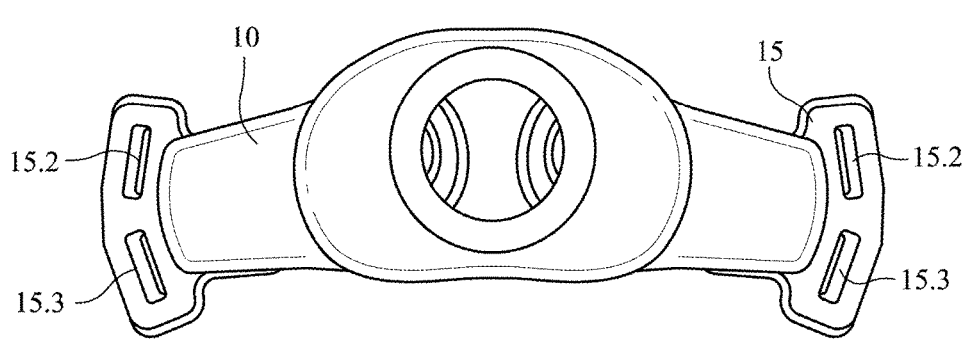
FIG. 12 is a rear view of the subcombination of the nasal interface and joining portions.
Figure 13:
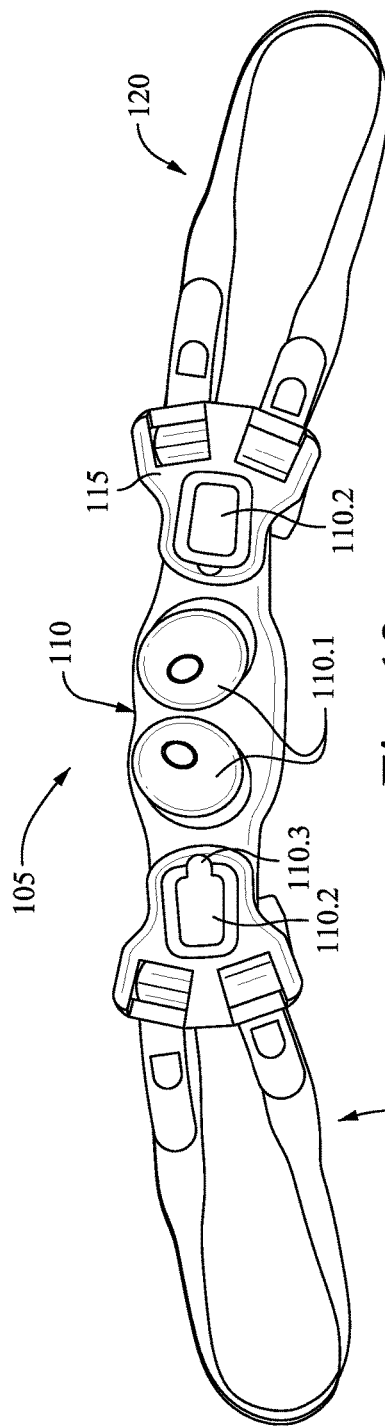
FIG. 13 illustrates an assembled front view of a mask assembly according to an example of the present technology.
Figure 14:
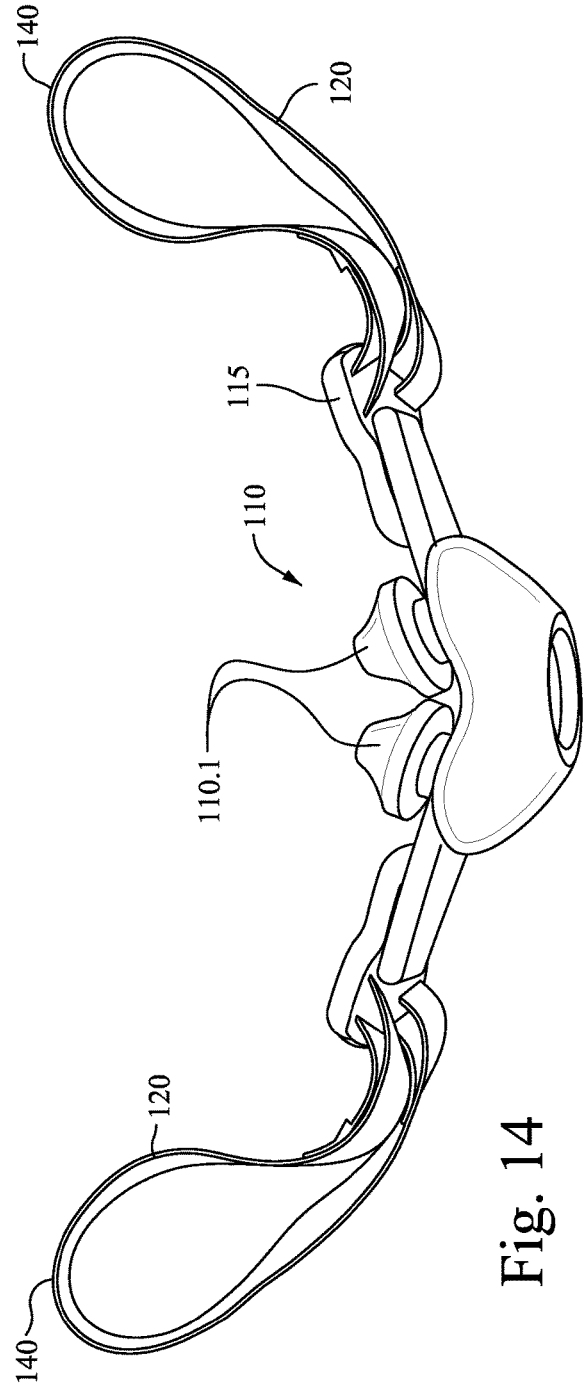
FIG. 14 is a top view thereof.
Figure 15:
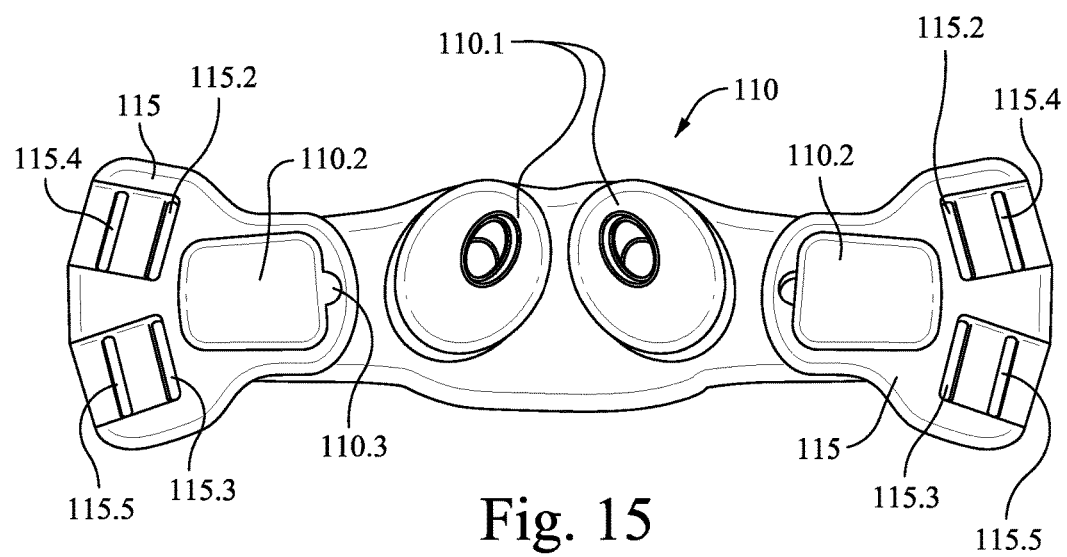
FIG. 15 is a front view of a subassembly of the nasal interface and joining portion shown in FIG. 13.
Figure 16:
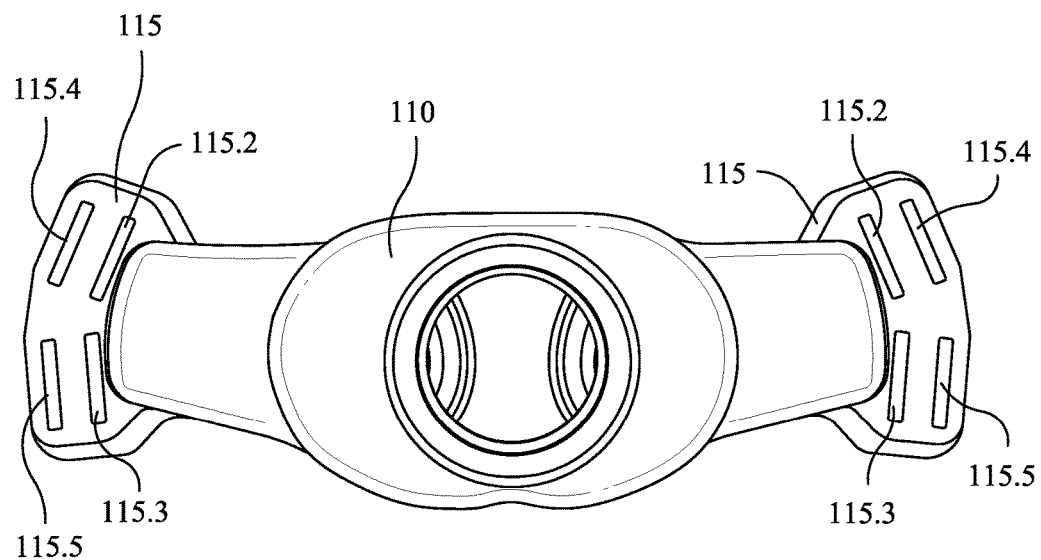
FIG. 16 is a rear view thereof.

FIG. 4 is an exploded view of the nasal interface 10 and respective joining portions 15 on the lateral sides of the nasal interface. The nasal interface includes a pair of nozzles 10.1 which have a generally truncated shape to anatomically match the patient's nose. In practice, the tip portion of each nozzle protrudes slightly within the patient's nose, while the broader base portion of each nozzle is intended to seal against the nares of the patient. As shown in FIG. 8, each nozzle includes an outer layer and an inner layer which is spaced from the outer layer to provide an enhanced cushioning and sealing effect. The seal, or nozzles 10.1 may include an elastic material. The nasal interface may include an aperture 10.5 to communicate with the elbow/short tube/air delivery tube.

Returning to FIG. 4, the nasal interface includes at least one lug 10.2 provided on each lateral side of the nasal interface. The nasal interface 10 shown in FIG. 4 substantially corresponds to the nasal interface sold with ResMed's Swift FX™ product. The left hand lug 10.2 includes an additional protrusion 10.3 which is intended to differentiate the left hand lug from the right hand lug and so that the headgear associated with the Swift FX™ mask, which includes left and right hand strap portions, can be assembled in the proper manner.

Each joining portion 15 includes a receiving portion 15.1, otherwise referred to as an attaching or an attachment portion. Each joining portion also includes an upper slot 15.2 and a lower slot 15.3 which may be separate from one another or be formed as a continuous slot.

The slots 15.2 and 15.3 may be angled (angle α) relative to one another, e.g., about 0-20° relative to horizontal. The included angle (β) between the first and second slots may be about 140-180°. See FIG. 6.

The receiving portion 15.1 of each joining portion 15 is intended to receive a corresponding lug 10.2 of the nasal interface.

Figure 5:
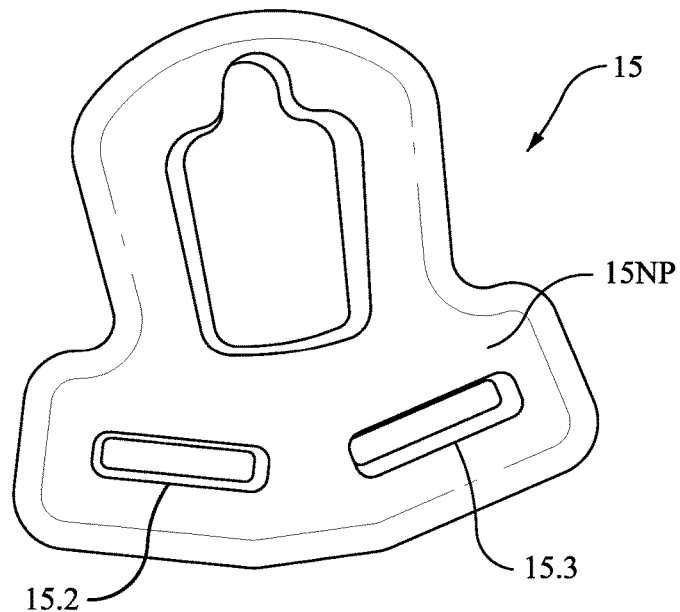
FIG. 5 is a view of a non-patient contacting side of a joining portion according to one variant of the present technology.
Figure 6:
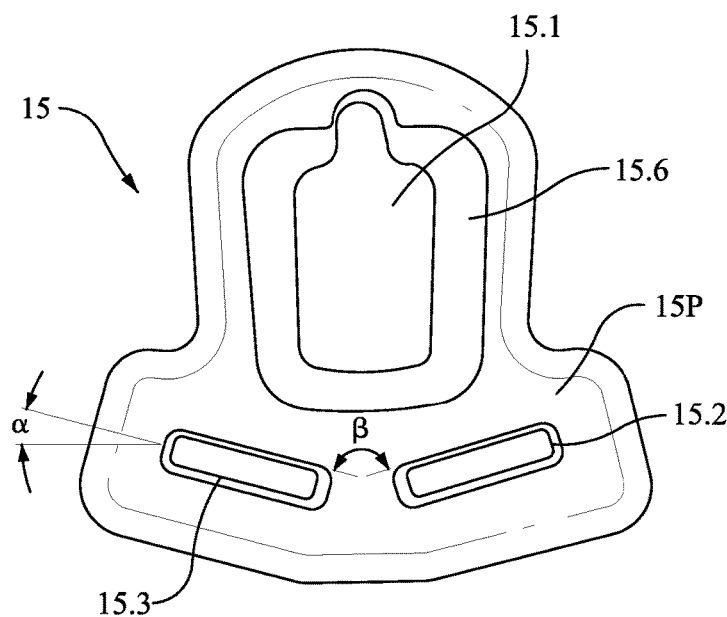
FIG. 6 is a front view of a patient contacting side of the joining portion shown in FIG. 5.
Figure 7:
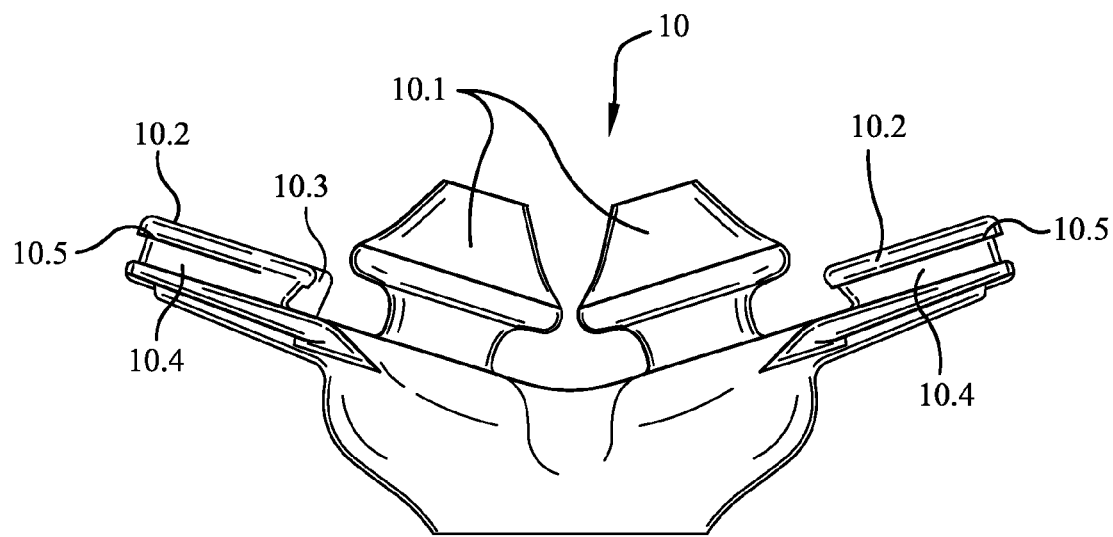
FIG. 7 is a side view of the nasal interface of FIG. 4 in isolation.

FIG. 5 shows a non-patient contacting side 15NP of the joining portion 15, while FIG. 6 shows a patient contacting side 15P of the joining portion 15. FIG. 7 shows a side view of the nasal interface 10, which in particular shows that each lug 10.2 includes a groove 10.4 defining an enlarged bead portion 10.5 of each lug. The enlarged head portion is intended to rest against a recess portion 15.6 shown in FIG. 6. In addition, attention is directed to FIG. 8 which shows a cross-section of the subcombination of the nasal interface 10 and joining portions 15.

FIGS. 9-12 show various orientations of the subcombination of the nasal interface 10 and joining portions 15. As is evidenced from FIGS. 8-12, the lugs 10.2 of the nasal interface include an upper surface that is essentially flush with the surrounding surface of the respective joining portion 15.

In addition, it is noted that each joining portion 15 has been provided with a recess 15.7 in order to accommodate the protrusion 10.3 of the nasal interface. As such, unlike ResMed's Swift FX™ mask, either joining portion can be attached to either lug of the nasal interface, as both joining portions will accommodate the protrusion 10.3 of the lug.

Figure 1:
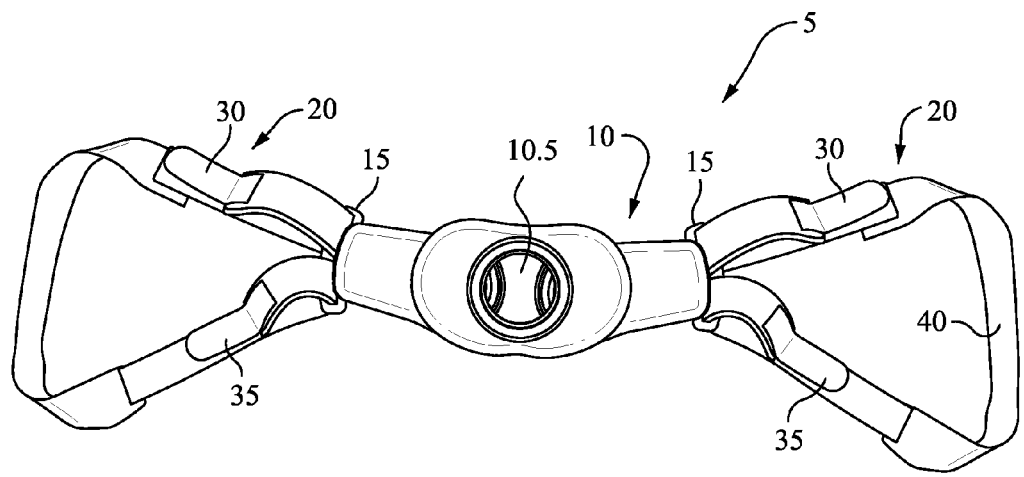
FIG. 1 is a front view of a mask assembly according to a first example of the present technology.
Figure 2:
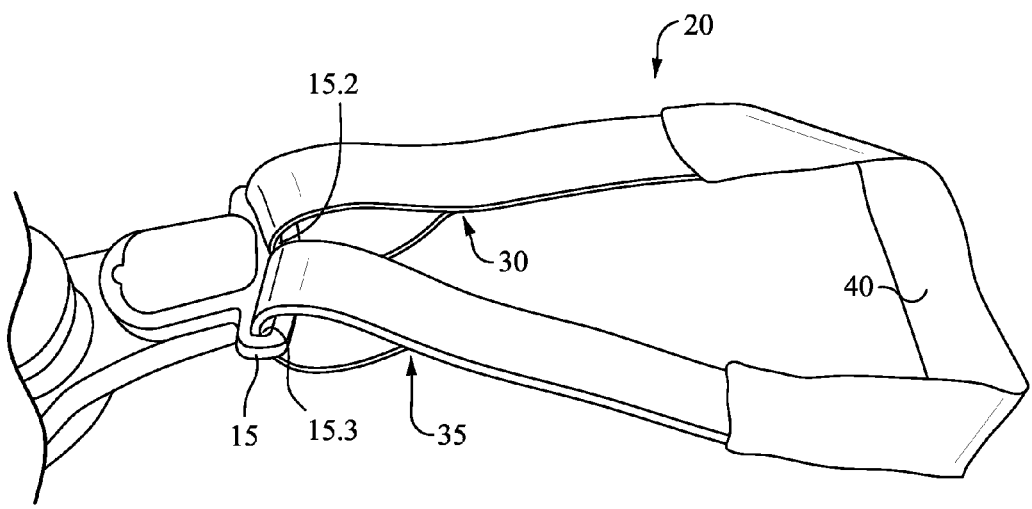
FIG. 2 is an enlarged view of the right hand side of the mask assembly shown in FIG. 1.

As best shown in FIG. 2, the headgear 20 may include first and second strap portions that terminate in strap ends 30 and 35, respectively. The first strap end 30 is threaded through the upper slot 15.2 while the second strap end 35 is threaded through the lower slot 15.3. The straps can be made from a composite material including two or more layers, e.g., three layers including a soft layer to contact the patient's face, a middle layer made of foam, and a loop material portion to receive a hook material portion of the strap ends as best shown in FIG. 1. In this way, the headgear can be length adjustable. However, aside from hook-and-loop, the headgear can be length adjustable in other manners, as described below. As shown in FIG. 2, the headgear 20 may include upper and lower straps that are made of a textile material, whereas the rear portion 40 of the headgear is made up of a plastic or textile material.

Adjustability may be enabled by allowing at least a portion of the headgear to be stretchable, like an elastic or rubber band.

As an alternative, the straps can take the form of a strap 230 as shown in FIG. 26. In FIG. 26, the strap includes a series of ridges 230.2 (provided on one or both sides of the front and rear sides of the strap) adapted to provide a lock or interference with the slots 15.2 or 15.3. The headgear may include a relatively larger ridge or stop 230.6 provided closer to the first and/or second ends of the strap, as shown in FIG. 26. It should be noted that the strap 230 shown in FIG. 26 can be used in the main examples or variants shown herein, e.g., in FIGS. 1-12, 13-22, 24 and 25 or other variants/examples described below.

As shown in FIG. 26, the strap may include a relatively thin and/or flexible region 230.1, compared to the remainder of the first strap. This region 230.1 may be provided in the center of the headgear, and is dimensioned to easily fit behind the patient's ears for more flexibility and comfort. Thinner and more flexible straps are able to fit into the crease behind the ear more readily and distribute forces evenly across the behind the ear region.

The ridges 230.2, 230.6 may provide the patient with tactile feedback as to the position of the strap in relation to the joining portion. The larger ridge or stop 230.6 may also be large enough to prevent the patient from removing the straps from the slots of the joining portion, i.e., a permanent one-way assembly.

The strap may be made of a variety of materials, including silicone, polypropylene, nylon, thermoplastic elastomer (TPE), and/or a thermoplastic polyurethane (TPU) material.

It should be noted that the joining portion 15 and the strap 20 may be made of a single piece or two or more individual pieces. As such, the joining portion 15 and the headgear 20 may be integrally formed or molded. The joining portion and the headgear may be made of a common material and that common material may have a variable hardness such that the first strap and the first joining portion have different hardnesses. In addition, the joining portion may include a first material and the strap may include a second material that is different from the first material.

A second main example of the present technology is illustrated in FIGS. 13-22. In these figures, the nasal interface 110 and the headgear 120 are similar to those described above. In addition in these figures, mask assembly 105, nozzles 110.1, lug 110.2, protrusion 110.3, and rear portion 140 are similar to those described above.

Figure 19:
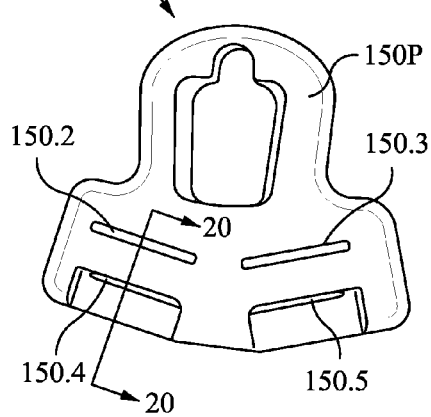
FIG. 19 is a front view of the patient contacting side of the joining portion shown in FIG. 13.
Figure 20:
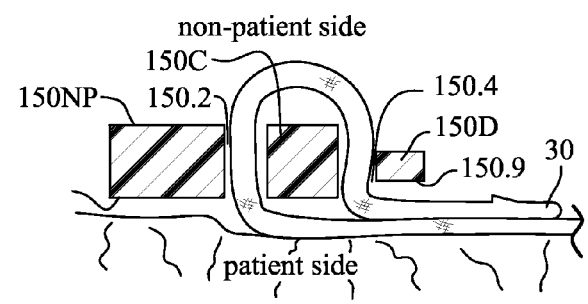
FIG. 20 is a schematic cross-sectional view taken along line 20-20 of FIG. 19.

The main difference relates to the joining member 115. In particular, the joining member includes four slot portions, including a pair of upper slot portions 115.2 and 115.4 and a pair of lower slot portions 115.3 and 115.5. In other words, each joining portion 115 includes four slot portions. FIGS. 15-18, 21 and 22 show a first variant of the joining portion 115, while FIGS. 19 and 20 show a second variant of the joining portion 150. FIGS. 19 and 20 also show a second variant of a pair of upper slot portions 150.2 and 150.4 and a pair of lower slot portions 150.3 and 150.5.

Figure 17:
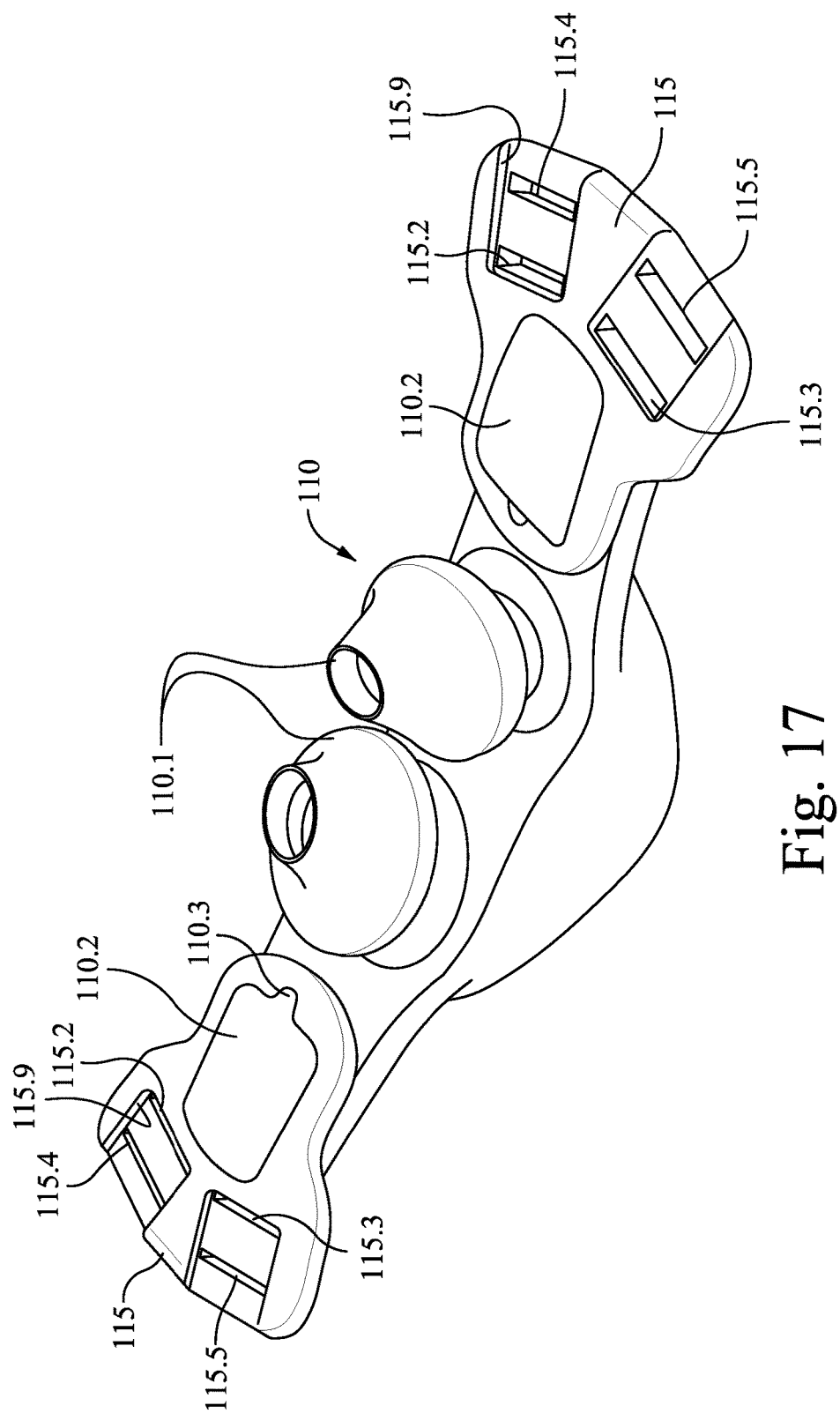
FIG. 17 is a perspective view thereof.
Figure 18:
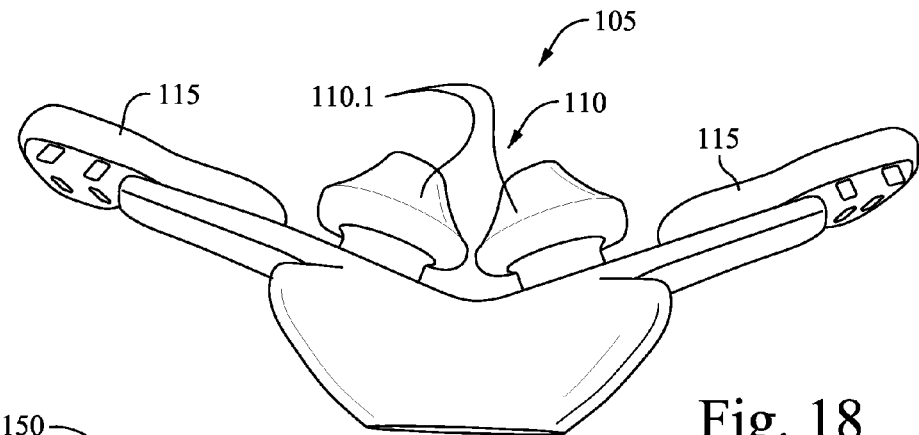
FIG. 18 is a top view of the subassembly.
Figure 21:
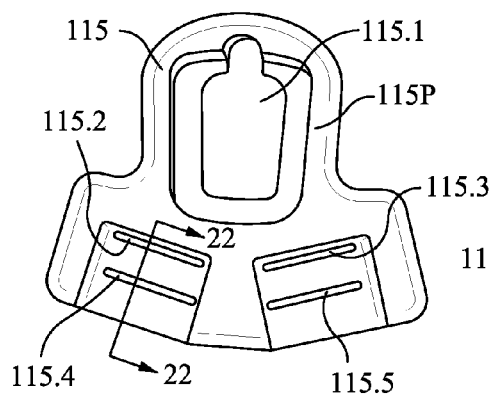
FIG. 21 is a front view from the patient contacting side of a joining portion according to a variant of the present technology.
Figure 21A:
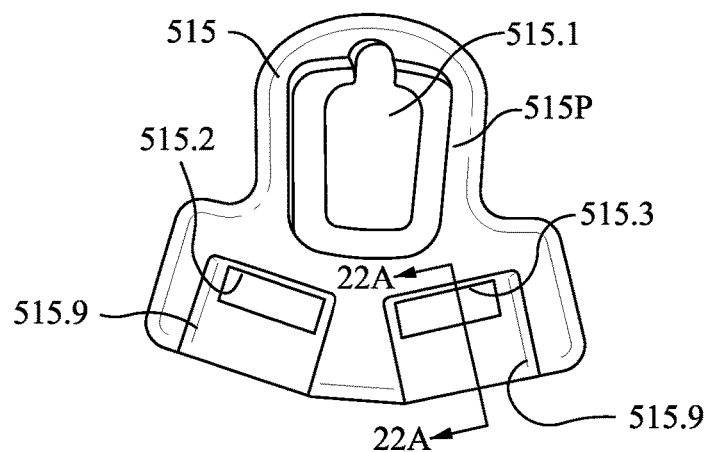
FIG. 21A is a front view from the patient-contacting side of a joining portion according to another variant of the present technology.
Figure 22A:
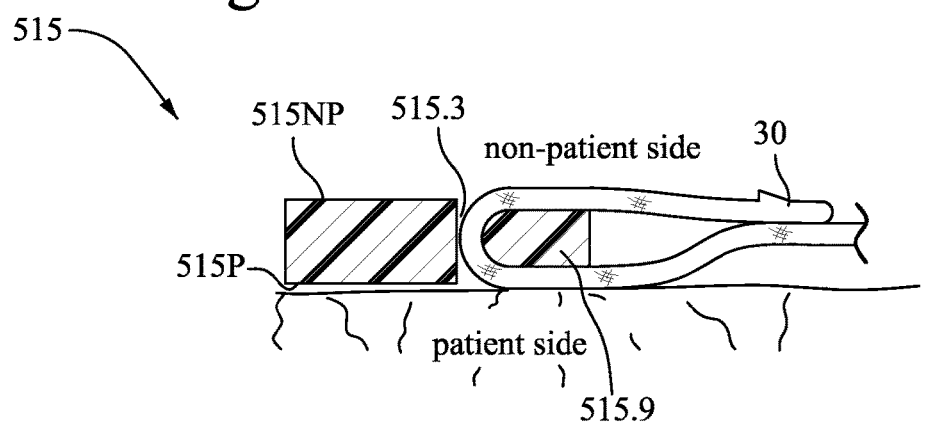
FIG. 22A is a schematic cross-section taken along line 22A-22A of FIG. 21A.

The provision of a pair of upper slots and a pair of lower slots allows the first end 30 of the strap to be threaded through the upper slots, and the second end 35 to be threaded through the lower slots, in order to form a ladder lock arrangement. In particular, per FIG. 22, the first end 30 of the first and second straps is threadable through the slot 115.2 that is closer to the attaching portion 115.1 in a direction extending from a patient's side 115P towards a non-patient side 115NP of the first and second joining portions, each first end 30 is then threadable through the other, i.e., 115.4, of the upper slots that is remote from the attaching portion 115.1 in a direction extending from the non-patient side 115NP to the patient side 115P. As best shown in FIGS. 17 and 21 and the cross-section of FIG. 22, the joining portion 115 include a relief portion 115.9 which is sufficient to accommodate the thickness of the strap, especially when the strap is doubled or folded over itself. This is shown in FIG. 22. FIGS. 21A and 22A show another variation including joining member 515, patient side 515P, non-patient side 515NP, attaching portion 515.1, an upper slot portion 515.2, a lower slot portion 515.3, and a center section 515.9

The variant shown in FIGS. 19 and 20 also include an upper pair and a lower pair of slots. FIGS. 19 and 20 also show a second variant including a patient side 150P and non-patient side 150NP. However, FIGS. 19 and 20 do not include a relief in the center section 150C which is between the slots 150.2 and 150.4. However, the distal end 150D of the joining portion may include a relief 150.9 that at least accommodates one of the two layers of the strap that are doubled over one another. See FIG. 20.

FIG. 23 shows a mask assembly according to a variant of the present technology. Mask assembly 305 includes a nasal interface 310 having a pair of nozzles 310.1 as described above. In addition, mask assembly 305 includes a pair of joining portions 315 which are attached to lugs of the nasal interface 310 as described above. The mask assembly 305 also includes headgear 320 provided to each of the joining portions 315. In this example, the joining portion 315 and the headgear are provided in one integral piece. In addition, the headgear includes first and second strap portions each having a respective end extending from the joining portion. One of the strap portions has a second end with a slotted connector 320.1, and the other of the first and second strap portions has a second end that is threaded through the slotted connector in a length adjustable manner. In particular, the slotted connector includes a base wall 320.2, a pair of side walls 320.3 and a cross portion 320.4 which together define a slot through which the strap extends. The strap includes a series of ridges (as described above) adapted to provide a lock or interface as the strap is threaded through the slot. In this particular case, only one of the straps is adjustable. A portion of the first and/or second strap portions has a rear portion 340 that is structured and dimensioned to be secured to the wearer's ear in use, as described above.

FIG. 24 shows a mask assembly 405 according to another example of the present technology. In FIG. 24, the nasal interface 410 is similar to those described above. FIG. 24 also includes first end 430, second end 435, and rear portion 440. In addition, the mask assembly 405 includes joining portions 415 which in this example includes a slotted connector similar in structure to the one described in relation to FIG. 23. However, in FIG. 24, it is the joining portion 415 that includes the slotted connector, which slotted connector forms a common slot for receipt of each end of the headgear 420. In particular, each strap end includes a series of protrusions, such that each strap end is movable relative to the common slot in a length adjustable fashion. The slotted connector including the common slot includes a receiving or attaching portion which attaches the respective lugs provided on the nasal interface, as described above. This is best shown in FIG. 25.

Figure 27:
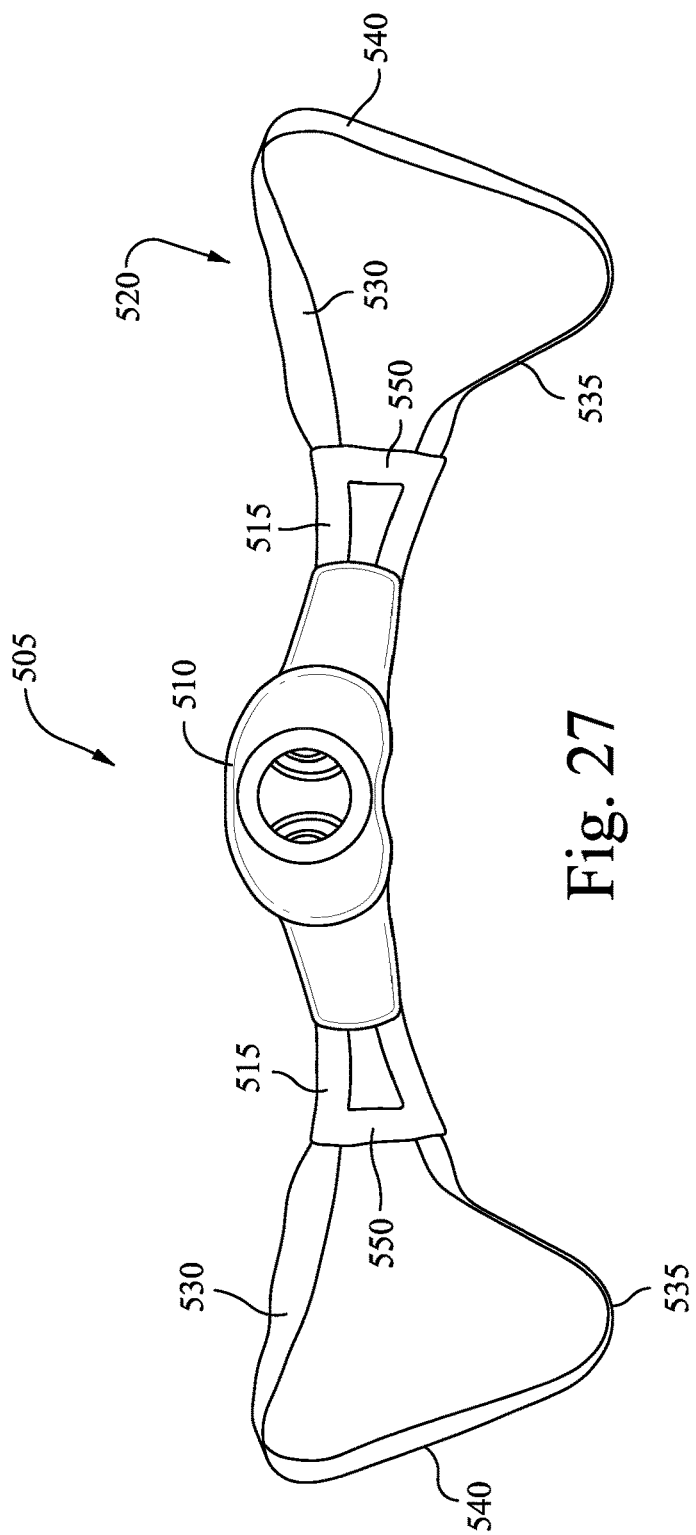
FIG. 27 illustrates a rear view of a mask assembly according to an example of the present technology.
Figure 28:
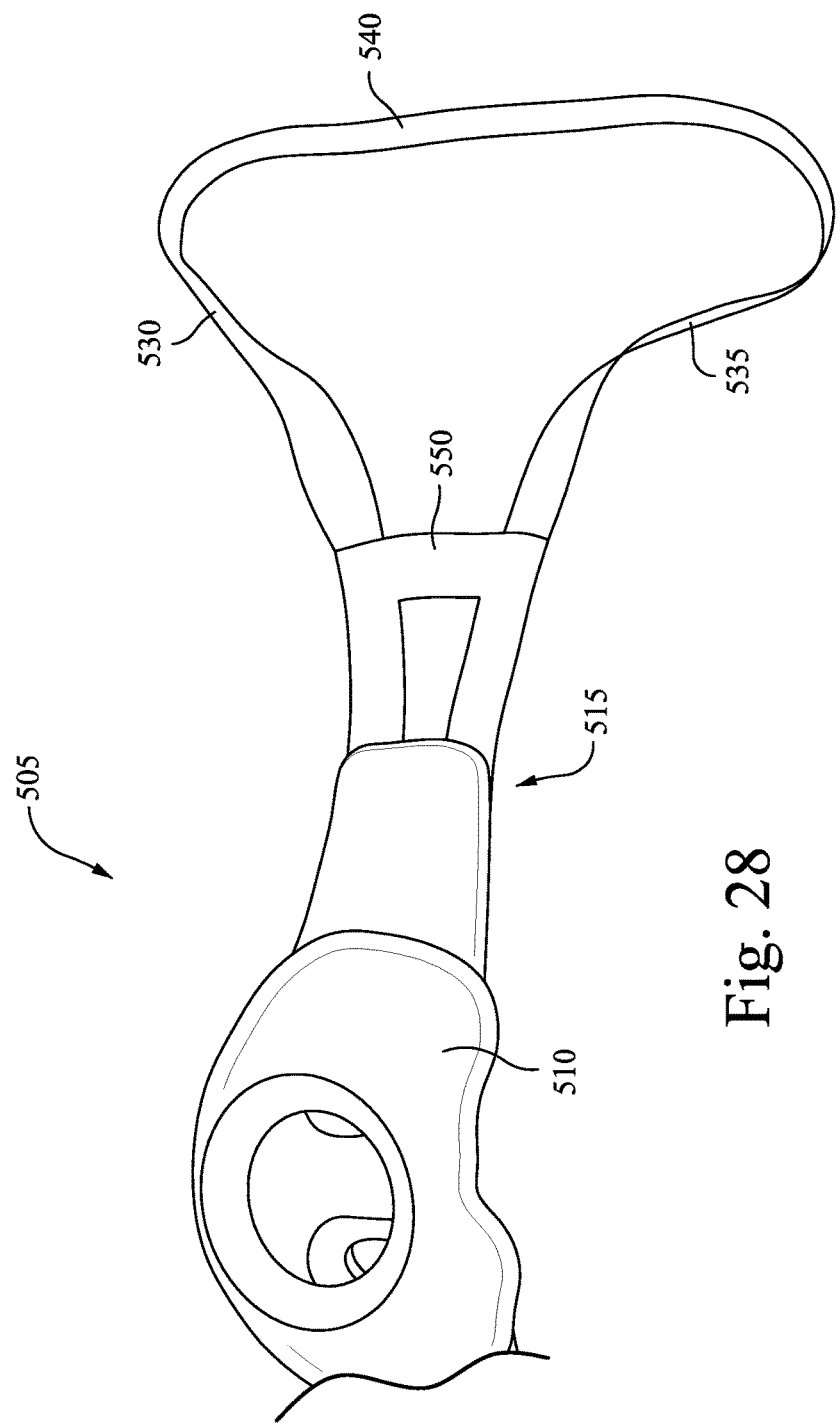
FIG. 28 is a partial enlarged view of a portion of the mask assembly shown in FIG. 27.

FIGS. 27 and 28 show a mask assembly 505 according to yet another variant of the present technology. In particular, mask assembly includes a nasal interface 510 similar to that described above. In FIG. 27, the mask assembly is shown as having a joining portion 515 as well as headgear 520. In the case of FIG. 27, the joining portion 515 and the headgear are formed in one piece or otherwise molded in one piece but made of similar or the same material. The subassembly of the joining portion and the headgear also includes a bridging member 550. The bridging member may cause the upper and lower strap to separate, in order to ensure that the straps are positioned at the vectors required for ensuring sealing of the seal portion of the nozzles relative to the patient's nares. FIGS. 27 and 28 according to this variant also show first end 530, second end 535, and rear portion 540.

Figure 29:
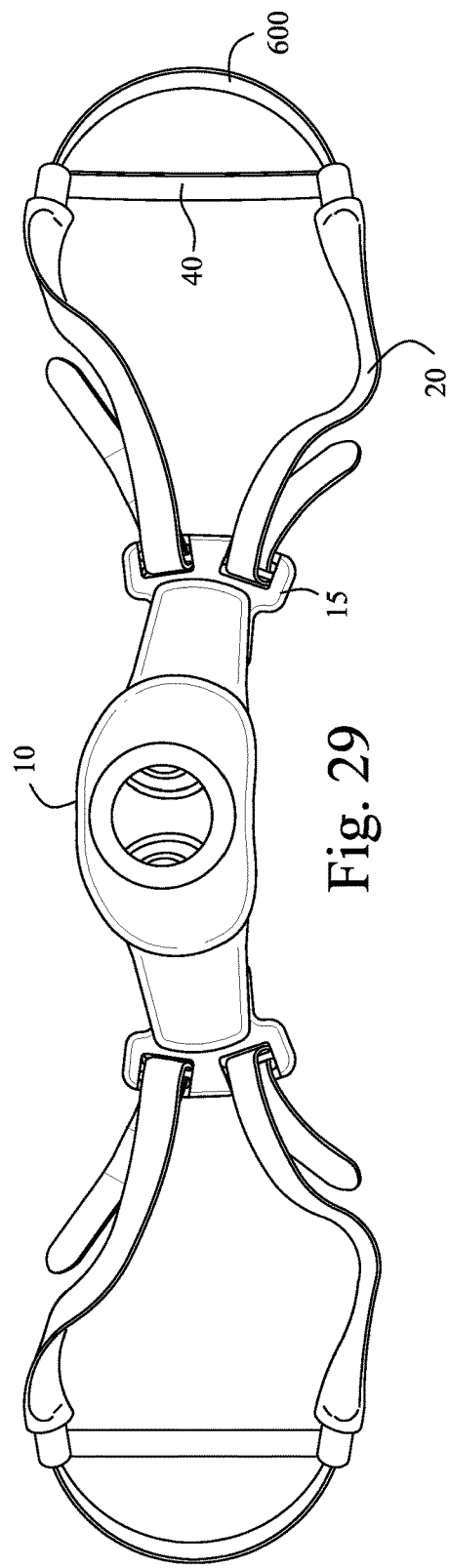
FIGS. 29 and 30 illustrate ear-gear according to variants of the present technology.
Figure 30:
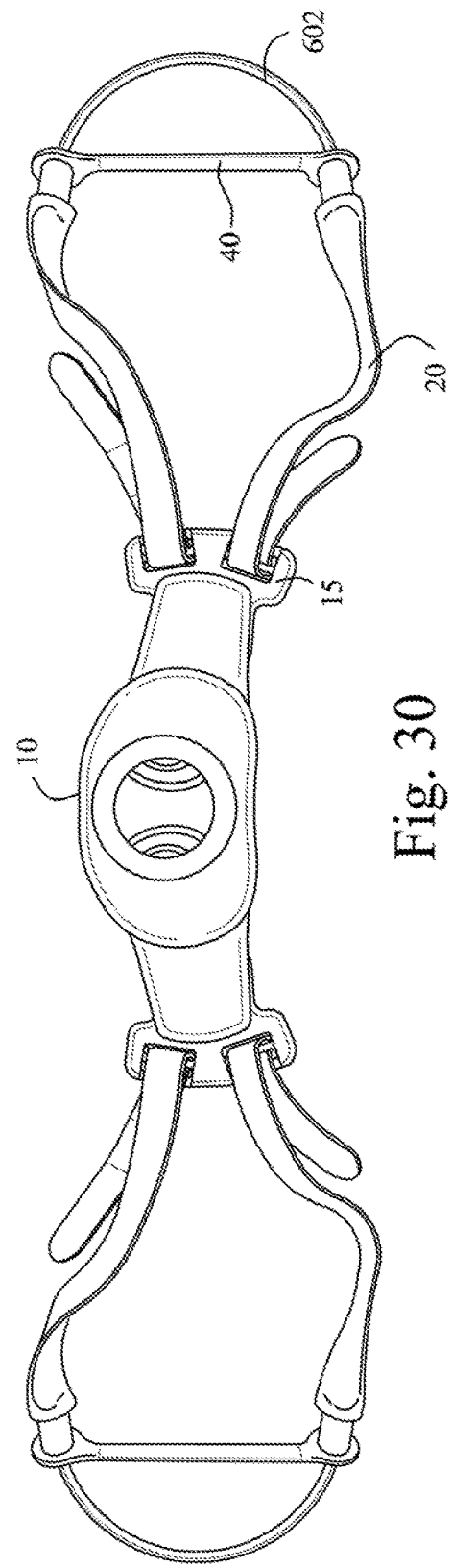
Figure 31:
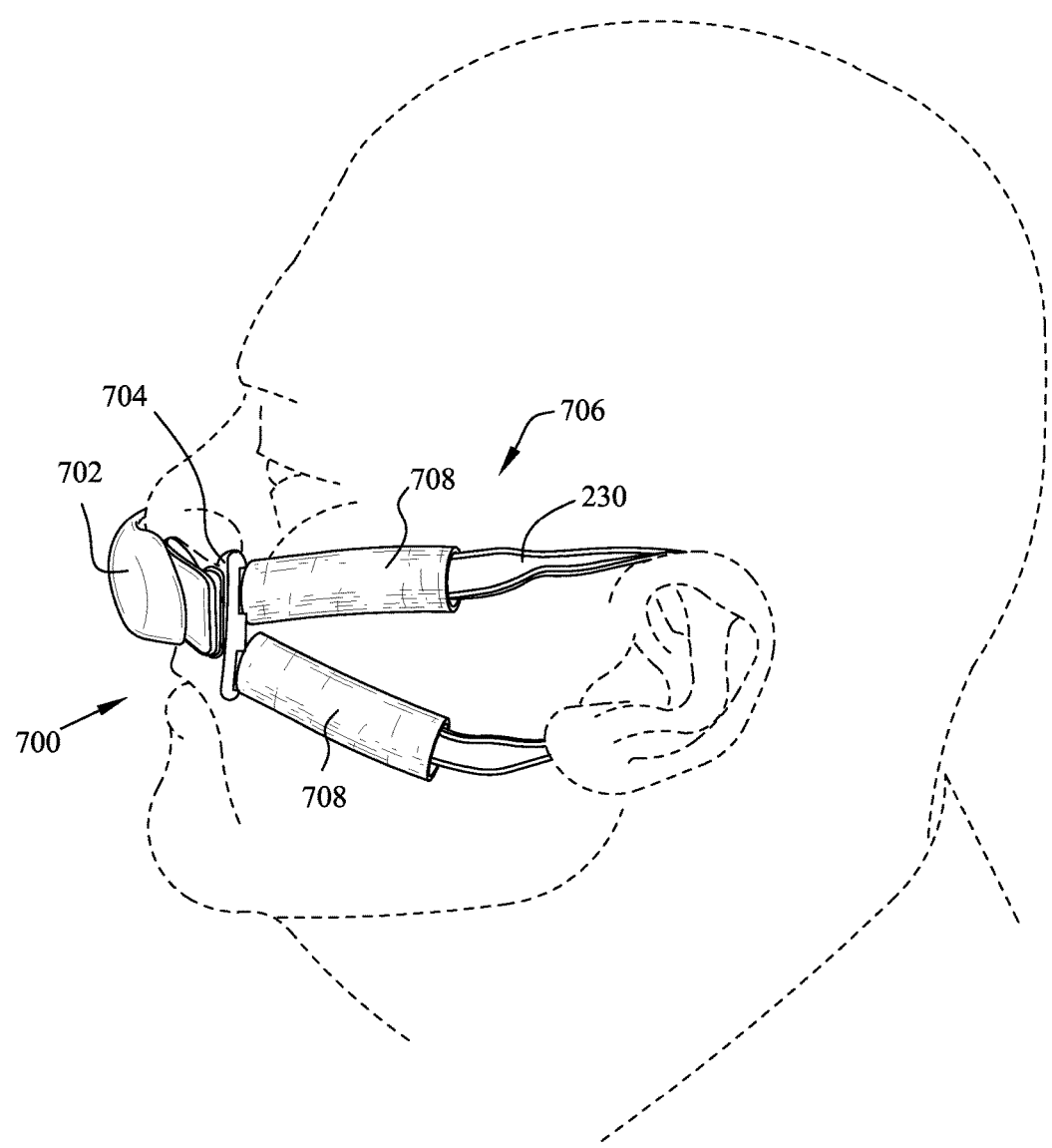
FIGS. 31-34 illustrate a mask assembly according to a variant of the present technology.

FIGS. 29-30 illustrate mask assemblies that include "ear-gear" having a rigidized component to provide comfort behind the ear and/or to reduce pressure spots on top and bottom of the ear. FIG. 29 illustrates ear-gear with a rigidized hard carrier 600 and FIG. 30 illustrates ear-gear with a rigidized spring carrier 602. Both involve over-molding wire or resin with silicone. Alternatively, the rigidized carrier may be removably attachable to the straps. Each rigidized component 600, 602 works in conjunction with a rear portion 40 of the strap. In use, both the rigidized component and the rear portion 40 of the strap are adapted to be positioned behind the ear. The spring carrier may distribute load around the back of the patient's ear more evenly and may reduce the force on the back of the ear translating a lower force on to the patient's ear (with some of the force being absorbed by the rigidized component). Preferably the rigidized component is stiffer than the strap.

FIGS. 31-34 illustrate a mask assembly 700 according to a variant of the present technology. Mask assembly 700 includes a nasal interface 702, a joining portion 704 and a headgear or ear-gear 706 which are similar to those described herein. For example, the ear-gear 706 may include the strap 230 as shown in FIG. 26.

In addition, the mask assembly 700, in particular, the ear-gear 706, includes at least one sleeve, preferably a pair of sleeves 708 through which the ends of the strap are threaded. The sleeves may be made of a soft material, such as a textile or fabric or lamination of materials, e.g., including textile and/or foam. The sleeve provides a level of comfort to the patient, e.g., to prevent or limit contact of strap with face and/or limit or prevent marks from the straps from appearing on the patient's face after long durations of use, e.g., 5-8 hours during the patient's sleep.

Each sleeve 708 may be made in a continuous cylindrical shape (e.g., 9-12 mm external diameter, e.g., 7-11 mm effective internal diameter, or cross-sectional dimension) with seamless construction. Alternatively, each sleeve 708 may take the form of a generally flat piece with the edges being fixedly or removably attached to one another. In the case of a fixed connection, the edges can be sewn together, while in the case of a detachable connection, hook and loop fastener may be employed.

Figure 32:
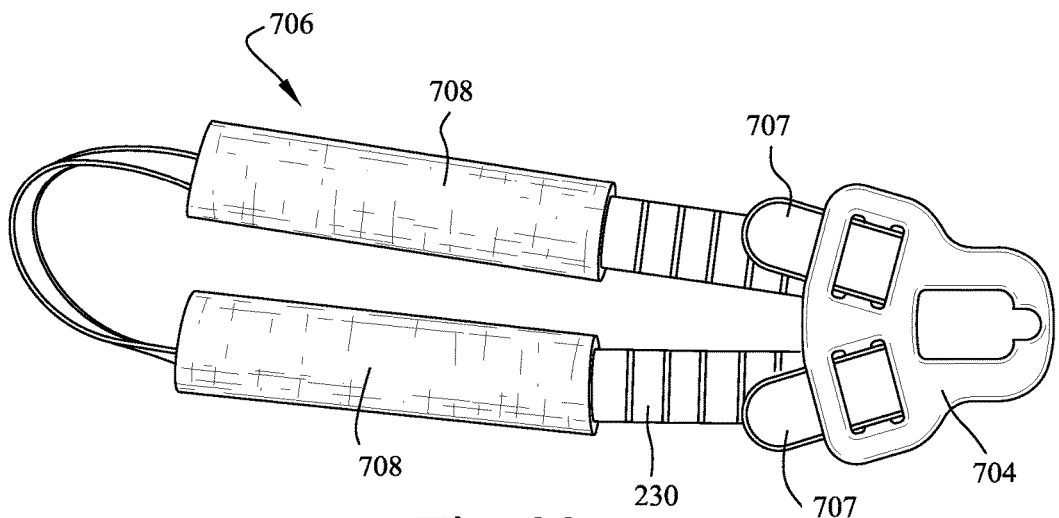
Figure 33:
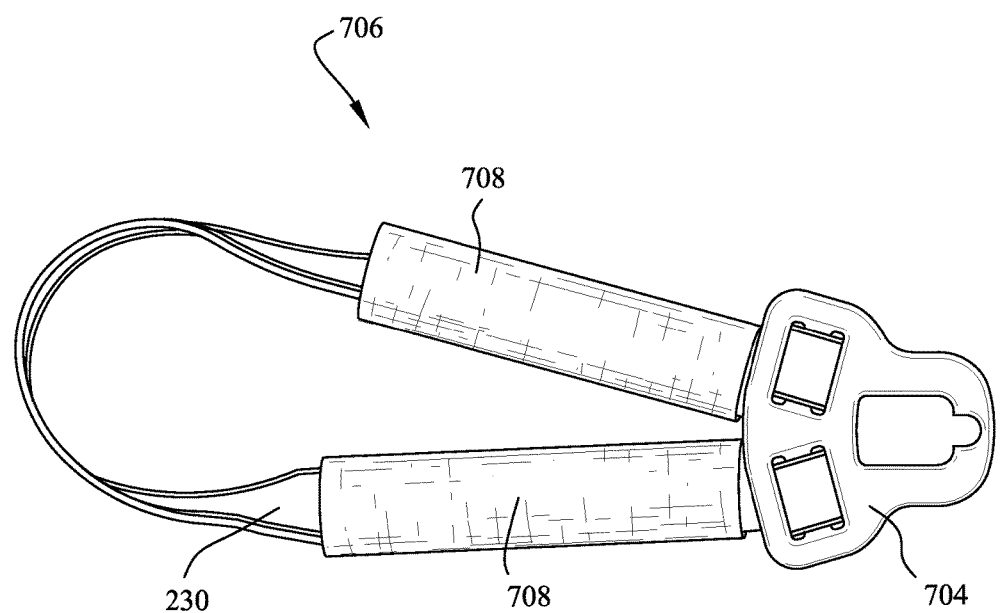
Figure 34:
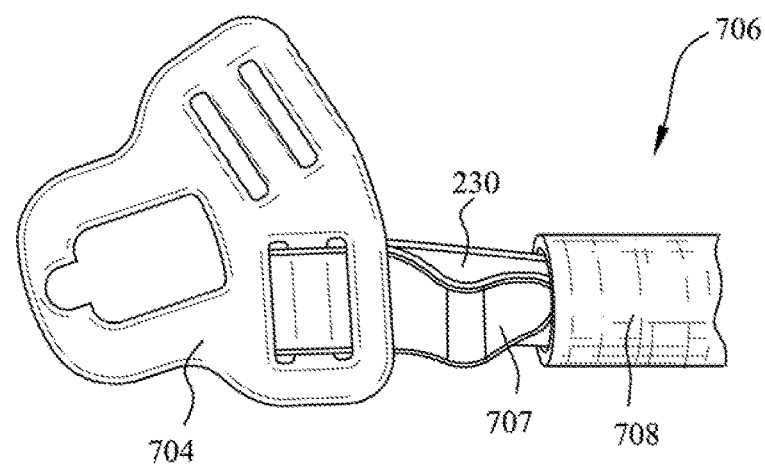

FIG. 32 shows the subassembly of the ear-gear 706 and joining portion 704. In the position shown, the tabs 707 of the strap have not been tightened, whereas in FIG. 33 the tabs 707 have been pulled more tightly, thus effectively shortening the total length of the straps, i.e., pulling the rear part of the straps toward the joining portion 704. FIG. 33 shows the position where the sleeves 708 are pushed forward towards the joining portion 704, so as to present a soft surface to engage the patient's cheeks once the straps extend beyond the joining portion 704. In FIG. 33, the tips or tabs of the straps have been tucked in or inserted through the sleeves to provide a neat and orderly appearance. FIG. 34 shows the tip or tab 707 of the strap being inserted into the sleeve 708.

Figure 35:
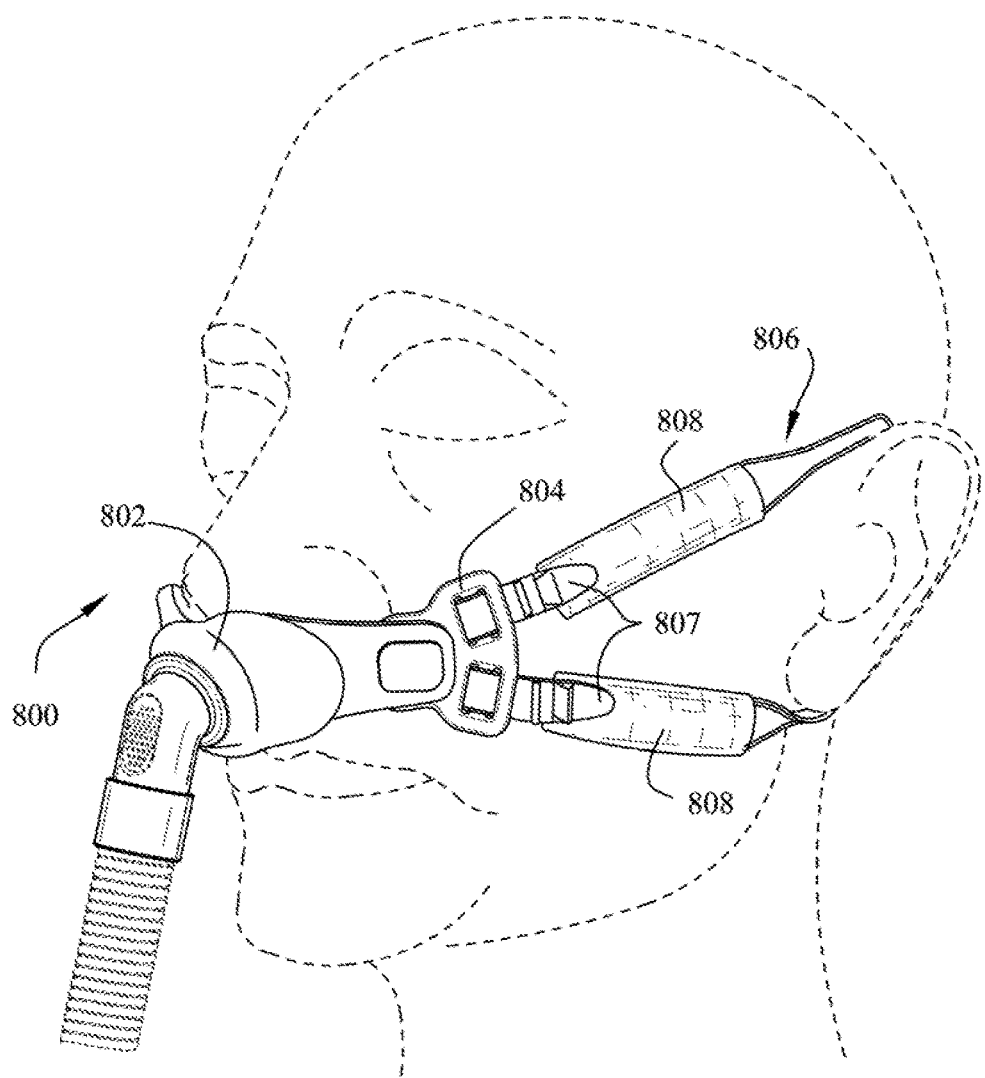

FIGS. 35-40 illustrate another variant according to the present technology. FIG. 35 shows a mask assembly 800 including a nasal interface 802, a joining portion 804 and ear-gear 806. The ear-gear 806 also includes sleeves 808 similar to those described above. However, in FIG. 35, the tips or tab 807 of the strap of the ear-gear have not yet been inserted into the sleeves 808.

Figure 36:
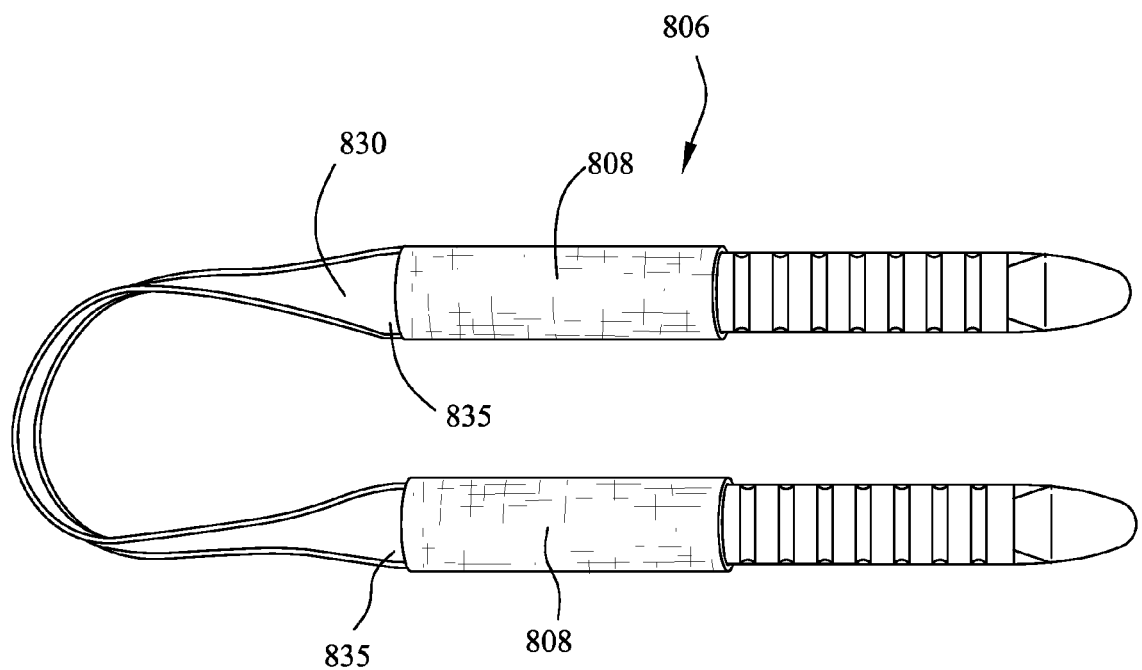

FIG. 36 illustrates a subassembly of the ear-gear 806, including the strap 830 as well as the sleeves 808 through which the tips of the straps have been inserted.

FIG. 37 illustrates the strap 830 while FIGS. 38 and 39 illustrate cross-sections of the strap.

In FIG. 35, the joining portion 804 may be made of a silicone having a hardness of 70 durometer Shore A. The joining portion may have an unfrosted surface, or it may have a frosted surface.

In regard to the strap 830, it includes a hardness of about 40 durometer Shore A. Further, the strap may be frosted. Frosting may be added to the straps or joining portion to improve feel, reduce friction, avoid sticking to the skin or to contrast with unfrosted surface markings such as branding.

The strap may be a silicone, silicone elastomer or compression grade silicone elastomer, e.g., available from Wacker under the Elastosil Rplus 4000, which has a durometer of about 40 Shore A.

As shown in FIG. 37, the strap 830 includes a center section 832 which is adapted to engage behind a rear portion of the patient's ears. As shown in FIG. 38, the center section may have a width w1 which is less than the width of the width w2 of the end portions of the strap (e.g., see FIG. 39) which are threaded through the joining portion. For example, the width w1 of the strap in the center section may be about 6 mm, while the width w2 towards the ends of the straps may be about 10 mm.

The center section 832 as shown in FIG. 38 has a non-constant cross section shape, e.g., a so-called "dog bone" shape in which at least one of the lateral ends 833 in cross-section has a thickness t1 which is greater than a thickness t2 of the center section 832 between or adjacent the lateral end(s). In an example, the thickness of the lateral ends 833 is similar to the thickness of the end portions of the strap. This shape is specifically effective to prevent tearing of the strap in this section. In addition, the reduced thickness of the strap helps it to be more comfortable to the patient as this portion of the strap is guided around the patient's ears.

The strap includes ladder lock sections 834 on each lateral end thereof, including a plurality of bumps or ridges 830.2 provided to the front and/or rear surfaces of the strap. Such bumps are shown on the front and rear sides of the strap as shown in the cross-section of FIG. 39. The bump height is between 1.5-1.75 mm, in this example.

As shown in the comparison between FIGS. 38 and 39, the ladder lock section of the strap does not include a dog bone shape, with such monolithic cross-section providing increased strength in this area.

Adjacent each ladder lock section 834 is a stop 835 of increased width provided to maintain the sleeves 808 in a predetermined position such that they will not drift or slide towards the patient's ears and away from the cheeks. In this example, the width of the stops 835 is about 10-15 mm, or anything greater than the width of the ladder lock sections and/or the effective internal dimension or diameter of the sleeves. Moreover, the stops serve as a transition point when transitioning from the waisted center section 832 toward the ladder lock section 834. When transitioning from the center section to the ladder lock section, the cross-section of the strap changes from the dog bone shape to the monolithic or regular substantially rectangular cross-sectional shape.

FIG. 37 also shows the tip portions 807 having an increased length so as to facilitate in threading the tips of the straps through the slots of the joining portions.

FIG. 37 also shows that the strap includes an end bump 809 which serves as an end stop such that the strap cannot be inadvertently removed from the joining portion. The end hump may be provided on one or both sides of the strap.

Figure 40:
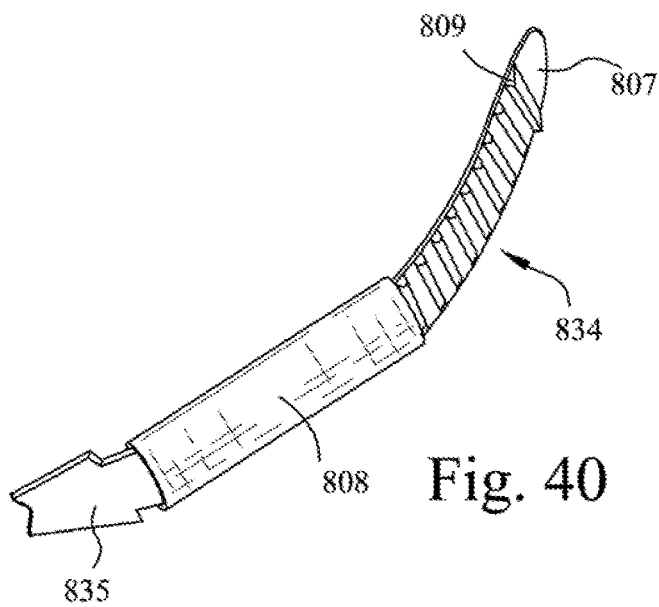

The strap may have a varying thickness along its length, e.g., from about 0.25 mm to 2 mm, or about 0.5 mm to about 1 mm. The straps may be thinner behind the ear region to reduce the load at the top and bottom of the ear and to permit greater flexibility and conformity of the strap at the back of the patient's ear. The straps may be thicker at the cheek region for load bearing, increased tear strength and reduced facial marking. FIG. 36 shows the strap in the position where the sleeves 808 have been attached. The sleeves 808 engage respective stops 835 such that the sleeves cannot slide or ride up towards the patient's ears in use. FIG. 40 shows an example in which a tip 807 of the strap has been threaded through the sleeve 808, and the sleeve has been pushed towards but is not yet engaging the stop 835.

Figure 41:
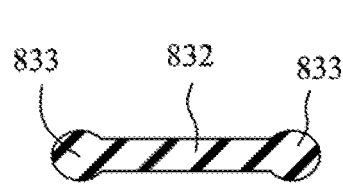
FIGS. 41-45 are cross-sections of ear-gear straps according to variants of the present technology.
Figure 42:
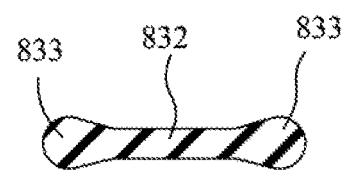

FIGS. 41-45 show various cross-sections of the strap along its length. For example, FIGS. 41 and 42 show various cross-sections of the center section 832, where the strap has a generally dog bone shape.

As shown in FIGS. 41 and 42, each lateral end 833 is in the form of a bead to increase the tear resistance of the strap. The bead may also reduce facial marking as the patient is in contact with a rounded edge rather than a sharp edge. As shown in FIG. 38, whereas the thickness t1 of the bead may be about 1 mm, the center section 832 has a thickness t1 of about half that, e.g., about 0.5 mm. The shape of the cross section shown in FIG. 41 demonstrates the heads of the dog bone 833 being distinct from the center section 832 i.e., there maybe a sharp transition between the head 833 and center section 832. The embodiment shown in FIG. 42 demonstrates a smoother transition between heads 833 and center section 832 where there is a sloping region that connects the heads 833 to the center section 832. Such an arrangement may be easier to manufacture, increase tear resistance and be more comfortable for the patient.

Figure 43:
Figure 44:
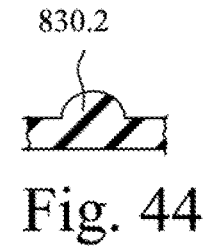
Figure 45:
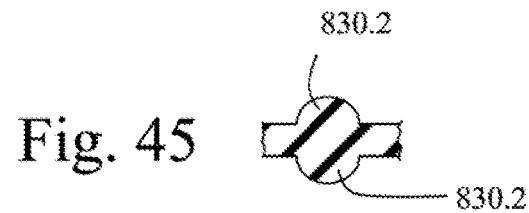

FIGS. 43-45 are cross-sections of the ladder lock section 834 of the straps. FIGS. 43 and 44 show the bumps 830.2 to be provided only on one side of the straps, whereas FIG. 45 shows the bumps 830.2 to be provided on both sides of the strap. FIG. 44 shows the case where the bumps have a sharp angled connection to the main body of the strap, whereas FIG. 43 shows the connection to be more rounded. The rounded connection may aid in increasing the tear resistance of the strap.

Bumps 830.2 may be provided on a single side of the strap or may be provided on both sides of the strap, such that the patient can align the straps in any orientation and there will be bumps on the outer side/non-patient side contacting side of the strap to aid in engagement with the joining portion.

As shown in FIG. 52, the strap may have a lead in 811 of reduced width and thickness, e.g., about 0.5 mm or varying thickness, e.g., from about 0.5-1 mm. The lead in may be tapered and may have a rounded end. Both of these attributes may aid the patient in engaging the strap in the slots of the joining portion.

Figure 46:
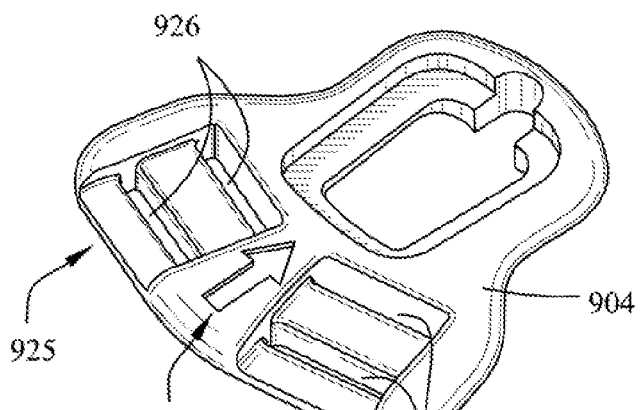
FIGS. 46-48 illustrate joining portions according to a variant of the present technology.
Figure 47:
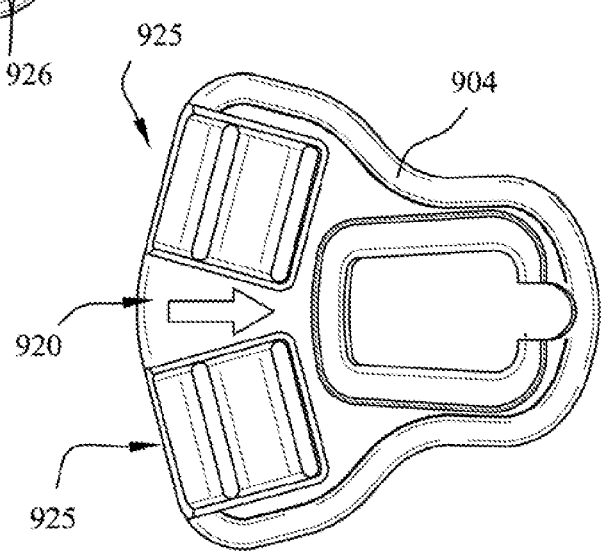
Figure 48:
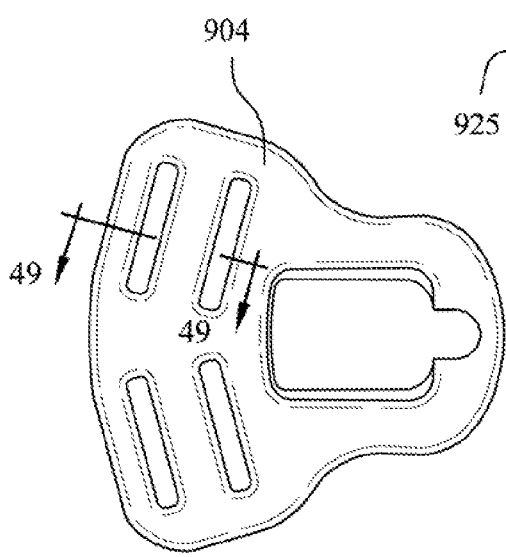
Figure 49:
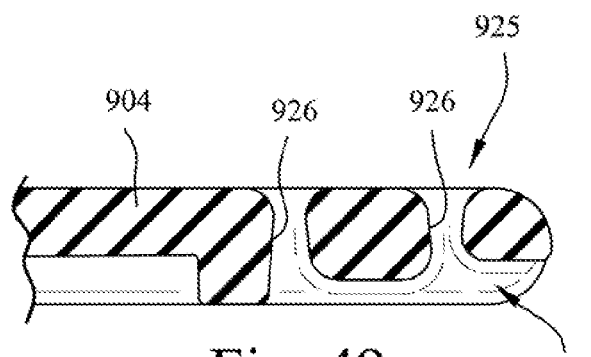
FIG. 49 is a cross-section taken along line 49-49 of FIG. 48.

As shown in FIGS. 46 and 47, an indicator 920, e.g., in the form of an embossed directional arrow may be provided between the ladder lock sections 925 of the joining portion 904 in order to aid in assembly. Furthermore, the outer profile variant maybe increased compared to the earlier described variants. FIG. 47 shows the patient contacting side of the joining portion 904, while FIG. 49 shows a cross-section along line 49-49 of FIG. 48 to show a ladder lock section 925. It is noted that the length of each slot 926 of the ladder lock section may be in a range of about 10.5 mm, or just slightly greater than the width of the straps.

The joining portion 904 may be a compression grade silicone material, e.g., available from Wacker under the Elastosil® Rplus 4000 with a durometer of about 70 Shore A. Such hardness helps to avoid twisting in use and when the strap is inserted through the slots. The slots 926 are tapered and have been radiused, as shown in the cross-section of FIG. 49 to ease assembly of the straps. The step 927 (see FIG. 49) has been increased for double strap thickness such that the strap lies flush with the surface of the joining portion and does not create a mark on the patient's cheek.

FIGS. 50-53 illustrate a strap 1030 according to another variant of the present technology. The strap includes a center section 1032 as well as a ladder lock section 1034 provided on each side of the center section. Again, the center section 1032 is intended to wrap around the back of the patient's ear, whereas the ladder lock sections 1034 are intended to be threaded through the joining portion, with the loose tip ends thereof being inserted through and into the sleeves for safekeeping. As best shown in FIG. 53, the center section 1032 has a width that varies between the stop portions 1035 for the sleeves. In the center, the center section has a width of about 6 mm, whereas at end sections or points P laterally outward of the center section, the width is about 10 mm, or about the same as the width as the ladder lock sections 1034. The transition between the 10 mm section and the 6 mm section is very gradual, to improve comfort. Each sleeve stop or stop portion 1035 has a width of about 10-20 mm, or about 14 mm.

Adjustment bumps 1030.2 were added to both sides (upper and/or lower surfaces) of the strap (e.g., see FIG. 51), each having total height of about 1.75 mm. Some of the adjustment bumps have been removed adjacent to the stops 1035, as it is unnecessary to have bumps where the sleeve is located. This also helps to avoid over tightening of the straps, dislodging of the sleeves 808 beyond the stop 1035, and reduces the marks on the patient's face. However, bumps may be provided along the length of the ladder lock sections to adjacent the stops as shown in FIG. 37. Stops 1009 have been added to both sides of the strap (e.g., see FIG. 51), both front and back, to ensure against inadvertent removal of the straps from the joining portions. In other words, the effective height of the stop has been doubled since it is provided on the front and back sides of each side of the strap.

Furthermore, compared to earlier examples, the tip 1007 of the strap has been further lengthened (e.g., see FIG. 52) to facilitate insertion into the joining portion.

Figure 54:
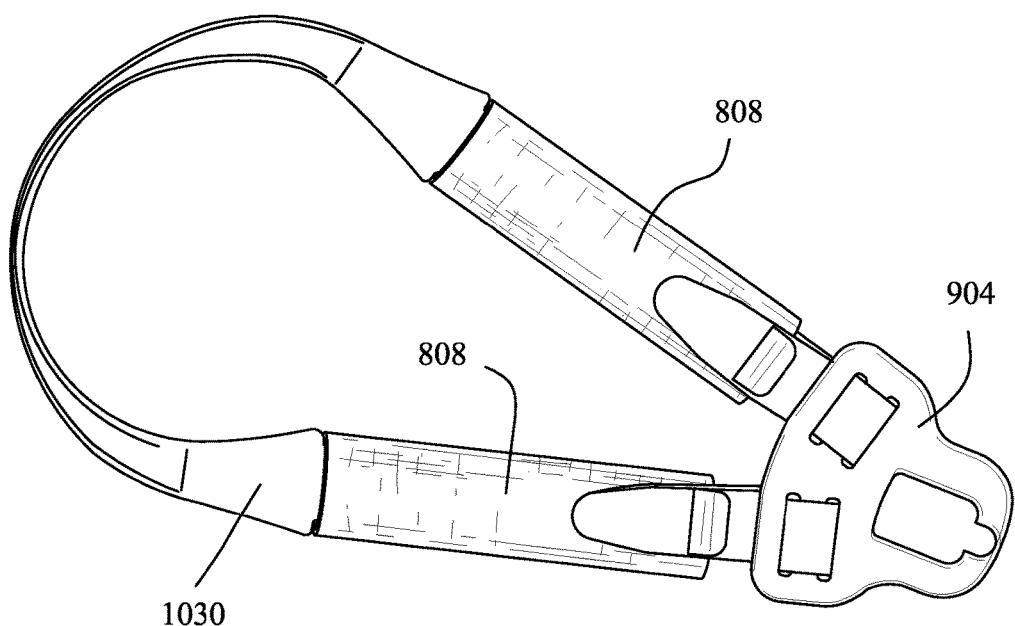
FIGS. 54 and 55 illustrate a subassembly of a strap, sleeve and joining portion according to a variant of the present technology.
Figure 55:
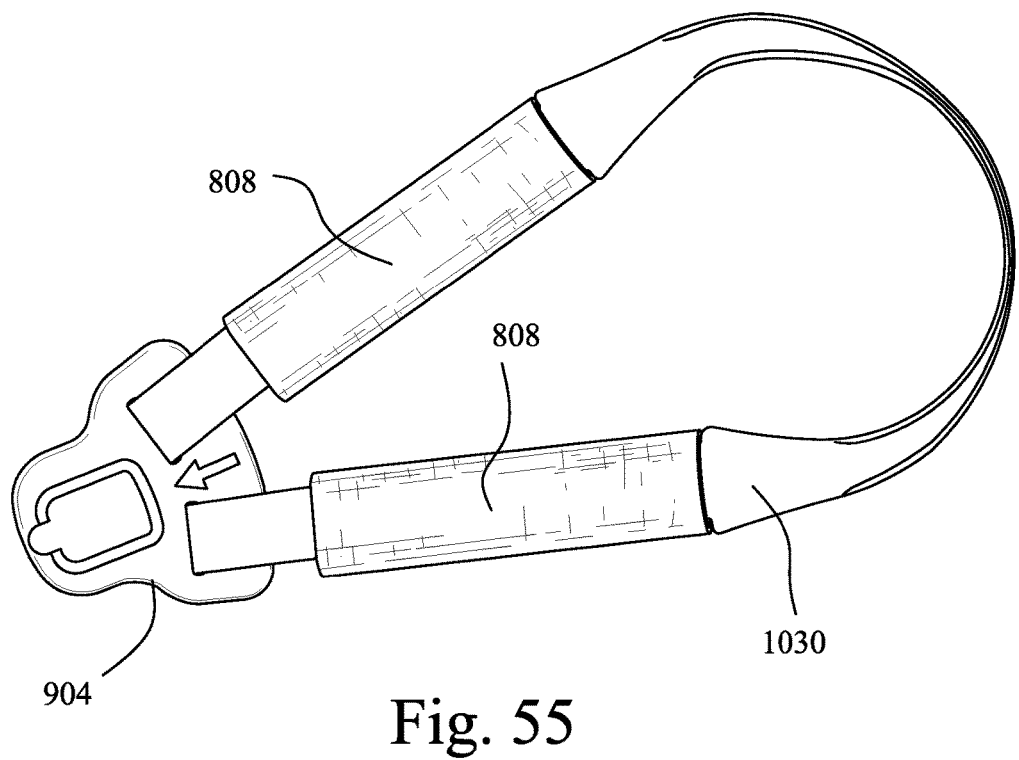
Figure 56:
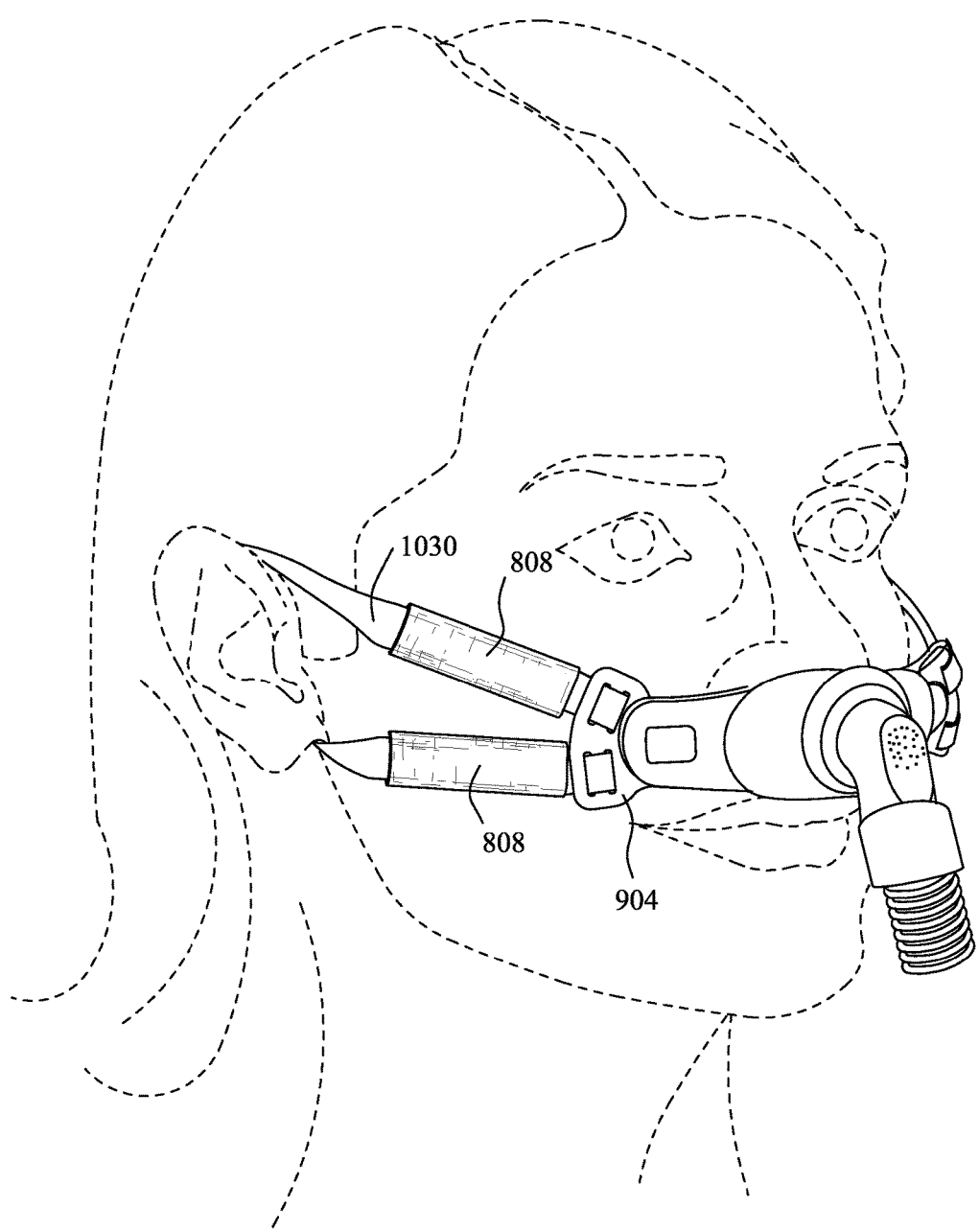
FIG. 56 illustrates the ear and mask assembly in position on a model patient's head according to a variant of the present technology.
Figure 57:
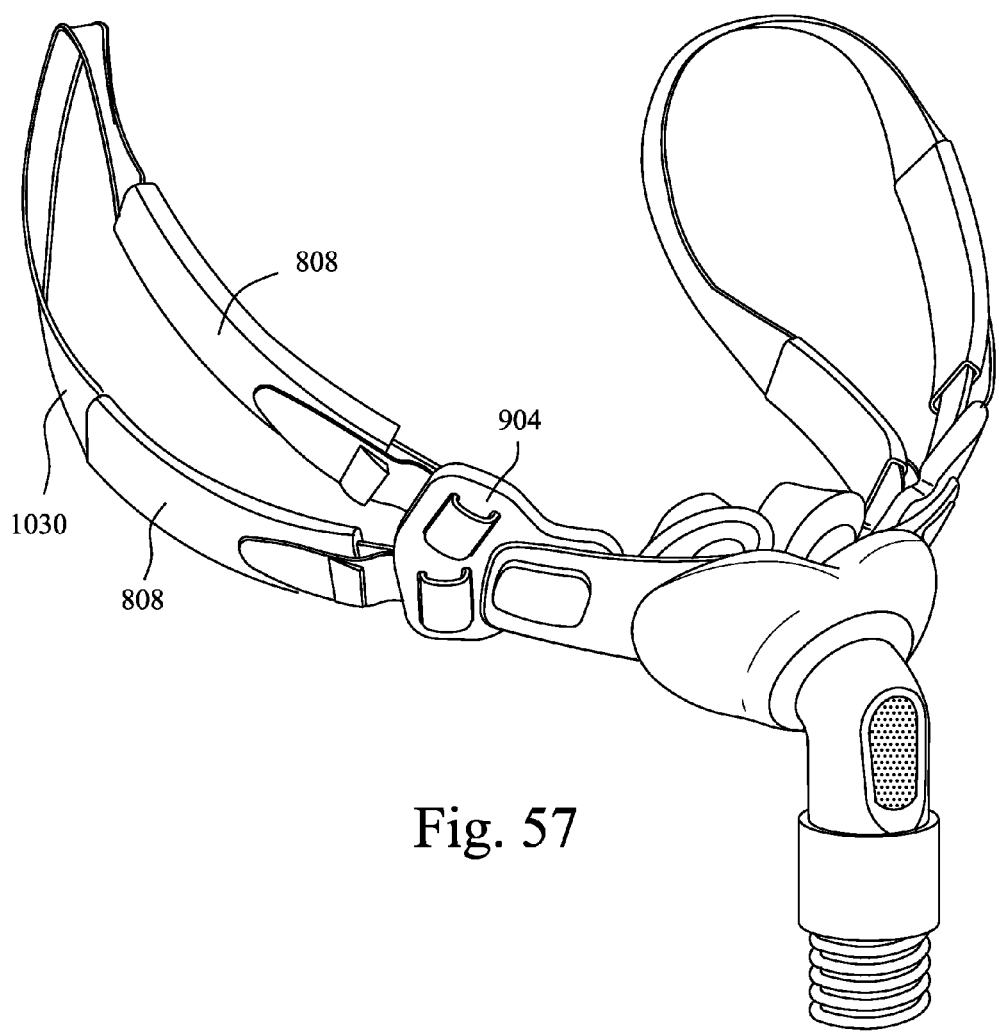
FIG. 57 illustrates a mask assembly according to a variant of the present technology.

FIGS. 54 and 55 illustrate views of the subassembly of the strap 1030, sleeve 808 and joining portion 904 while FIG. 57 illustrates the mask assembly in use, while FIG. 56 illustrates the mask assembly in isolation.

Figure 58:
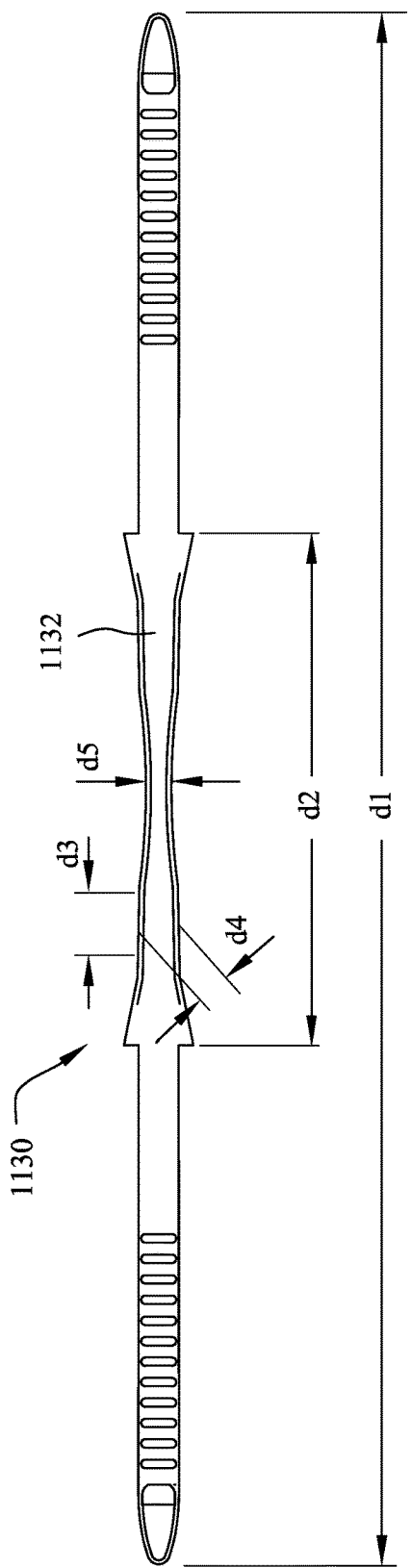
FIG. 58 illustrates an ear-gear strap according to a variant of the present technology.

FIG. 58 illustrates another variant of the strap 1130, which is similar to that shown in FIGS. 50-53. FIG. 58 shows exemplary dimensions of the strap, including an overall length d1 of about 380 mm, from tip to tip, whereas the center waisted section 1132 of the strap, e.g., from one stop to the other includes a length d2 about 125 mm. Furthermore, FIG. 58 shows a relatively wide portion over the top and/or bottom of the ear which extends over a length distance d3 of about 15 mm where the width d4 of the strap is about 10 mm. This 10 mm thickness tapers to a thickness d5 of about 6 mm in the center of the center section.

While the present technology has been described in connection with what are presently considered to be the most practical and preferred examples, it is to be understood that the present technology is not to be limited to the disclosed examples, but on the contrary, is intended to cover various modifications and equivalent arrangements included within the spirit and scope of the disclosure. In addition, while the present technology has particular application to patients/wearer's who suffer from OSA, it is to be appreciated that wearer's/patients who suffer from other illnesses (e.g., congestive heart failure, snoring, diabetes, morbid obesity, stroke, bariatric surgery, etc.) can derive benefit from the above teachings. Moreover, the above teachings have applicability with patients and non-patients alike in non-medical applications.

What is claimed is:

1. A headgear assembly for supporting a patient interface for treating a wearer having a breathing disorder with gas pressurized above atmospheric pressure, the headgear assembly comprising:
   first and second joining portions configured to be arranged on and removably attachable to opposite ends of the patient interface, each of the first and second joining portions having a patient interface attachment portion at a first end configured to attach to the patient interface, and a headgear attachment portion at a second end; and
   headgear having a first strap assembly and a second strap assembly, each of the first and second strap assemblies having:
      a first strap portion including:
         a first end that is removably attachable to the headgear attachment portion of the respective joining portion; and
         a second end that is attached to an ear interface assembly; and
      a second strap portion including:
         a first end that is removably attachable to the headgear attachment portion of the respective joining portion; and
         a second end that is attached to the ear interface assembly; and
      the ear interface assembly being structured and dimensioned to be secured to the wearer's ear in use.

2. The headgear assembly according to claim 1, wherein the ear interface assembly is removably attachable to the second end of the first strap portion and the second end of the second strap portion.

3. The headgear assembly according to claim 1, wherein the ear interface assembly comprises a carrier portion, the carrier portion extending from a first attachment point adjacent the second end of the first strap portion to a second attachment point adjacent the second end of the second strap portion.

4. The headgear assembly according to claim 3, wherein the ear interface assembly comprises a rear portion, the rear portion extending from the first attachment point adjacent the second end of the first strap portion to the second attachment point adjacent the second end of the second strap portion.

5. The headgear assembly according to claim 4, wherein the carrier portion comprises a curved configuration.

6. The headgear assembly according to claim 5, wherein the rear portion comprises a substantially linear configuration.

7. The headgear assembly according to claim 4, wherein the rear portion comprises adjustable length ear loops.

8. The headgear assembly according to claim 6, wherein the rear portion is adapted to be positioned behind the ear during use.

9. The headgear assembly according to claim 6, wherein the carrier portion is detachable from the first and second strap assemblies.

10. The headgear assembly according to claim 1, wherein the second end of the first strap portion and the second end of the second strap portion each comprise an ear interface assembly receiving structure.

11. The headgear assembly according to claim 1, wherein the ear interface assembly is stiffer than the first strap portion and the second strap portion.

12. The headgear assembly according to claim 1, wherein the ear interface assembly comprises silicon overmolding wire or resin.

13. The headgear assembly according to claim 1, wherein the first strap portion and the second strap portion are connected at a joining portion proximate end by a bridging member, the bridging member having a portion which extends in a direction transverse to a longitudinal direction of the respective strap portions.

14. The headgear assembly according to claim 1, wherein the first strap portion and the second strap portion are covered by a strap sleeve through which the respective strap portion is threaded, the strap sleeve being made of a soft material relative to the respective strap portion and configured to provide comfort while in contact with the wearer's skin during use.

* * * * *